US012611092B2

(12) United States Patent (10) Patent No.: US 12,611,092 B2
Ku et al. (45) Date of Patent: Apr. 28, 2026

(54) SYSTEMS AND METHODS FOR CONFIGURABLE ENDOSCOPE BENDING SECTION

(71) Applicant: Noah Medical Corporation, San Carlos, CA (US)

(72) Inventors: Vincent Ku, Palo Alto, CA (US); Daniel Louis Nasr-Church, San Diego, CA (US); Enrique Romo, Danville, CA (US); Hossein Dehghani, Dublin, CA (US)

(73) Assignee: Noah Medical Corporation, San Carlos, CA (US)

( * ) Notice: Subject to any disclaimer, the term of this patent is extended or adjusted under 35 U.S.C. 154(b) by 192 days.

(21) Appl. No.: 18/607,809

(22) Filed: Mar. 18, 2024

(65) Prior Publication Data

US 2024/0260820 A1 Aug. 8, 2024

Related U.S. Application Data

(63) Continuation of application No. PCT/US2022/043997, filed on Sep. 19, 2022.

(60) Provisional application No. 63/250,263, filed on Sep. 30, 2021.

(51) Int. Cl.
*A61B 1/005* (2006.01)
*A61B 1/00* (2006.01)

(52) U.S. Cl.
CPC ........ *A61B 1/0057* (2013.01); *A61B 1/00042* (2022.02); *A61B 1/00103* (2013.01)

(58) Field of Classification Search
None
See application file for complete search history.

(56) References Cited

U.S. PATENT DOCUMENTS

| | | |
|---|---|---|
| 5,478,330 A | 12/1995 | Imran et al. |
| 9,314,306 B2 | 4/2016 | Yu |

(Continued)

FOREIGN PATENT DOCUMENTS

| | | |
|---|---|---|
| WO | WO-2021127449 A1 | 6/2021 |
| WO | WO-2023055600 A1 | 4/2023 |

OTHER PUBLICATIONS

EP22877138.2 Extended European Search Report dated Jun. 10, 2025.

(Continued)

*Primary Examiner* — Mohammad J Rahman
(74) *Attorney, Agent, or Firm* — Wilson Sonsini Goodrich & Rosati

(57) ABSTRACT

An articulating flexible endoscope is provided. The endoscope comprises: a bending section connected to a distal tip portion at a first end, and connected to a shaft portion at a second end; a pull wire coupled to the distal tip portion at a first location and is configured for articulating the bending section; and a first tube for accommodating the pull wire. A distal end of the first tube is coupled to a second location on the bending section or on the shaft portion, a proximal end of the first tube is coupled to a proximal portion of the articulating flexible endoscope. An effective bending section of the articulating flexible endoscope is adjusted by varying i) a length between the first location and the second location or ii) the second location.

19 Claims, 30 Drawing Sheets

(56)                    References Cited

U.S. PATENT DOCUMENTS

| | | | | |
|---|---|---|---|---|
| 11,717,147 | B2 * | 8/2023 | Hsu | A61B 1/00087 |
| | | | | 600/135 |
| 11,759,605 | B2 * | 9/2023 | Romo | A61M 25/0012 |
| | | | | 604/526 |
| 11,925,316 | B2 * | 3/2024 | Harada | A61B 1/018 |
| 2006/0270975 | A1 | 11/2006 | Savage | |
| 2007/0239066 | A1 * | 10/2007 | Laham | A61B 17/3478 |
| | | | | 600/567 |
| 2009/0054733 | A1 * | 2/2009 | Marescaux | A61B 17/29 |
| | | | | 600/149 |
| 2009/0137875 | A1 | 5/2009 | Kitagawa et al. | |
| 2010/0280449 | A1 | 11/2010 | Alvarez et al. | |
| 2013/0178705 | A1 | 7/2013 | Takeuchi | |
| 2015/0032024 | A1 * | 1/2015 | Furlong | A61B 1/015 |
| | | | | 600/566 |
| 2016/0270866 | A1 * | 9/2016 | Yu | A61B 1/00147 |
| 2018/0049873 | A1 * | 2/2018 | Manash | A61M 25/09 |
| 2018/0214011 | A1 * | 8/2018 | Graetzel | G01B 21/16 |
| 2018/0360435 | A1 * | 12/2018 | Romo | A61B 1/0056 |
| 2019/0350607 | A1 * | 11/2019 | Martone | A61B 17/3201 |
| 2020/0129050 | A1 * | 4/2020 | Sinay | A61B 1/00128 |
| 2021/0369085 | A1 * | 12/2021 | Kato | A61M 25/0102 |
| 2022/0152356 | A1 | 5/2022 | Kowshik | |
| 2022/0202276 | A1 * | 6/2022 | Meglan | A61B 1/00117 |
| 2023/0165445 | A1 * | 6/2023 | Matthison-Hansen | |
| | | | | A61B 1/0055 |
| | | | | 600/141 |
| 2023/0284884 | A1 * | 9/2023 | Zhou | A61B 1/04 |
| 2023/0364404 | A1 * | 11/2023 | Kellogg | A61N 7/02 |
| 2023/0371786 | A1 * | 11/2023 | Wu | H02K 11/24 |
| 2024/0090753 | A1 * | 3/2024 | Lee | A61B 1/07 |

OTHER PUBLICATIONS

PCT/US2022/043997 International Search Report and Written Opinion dated Jan. 30, 2023.
PCT/US2022/043997 International Preliminary Report on Patentability dated Apr. 2, 2024.

* cited by examiner

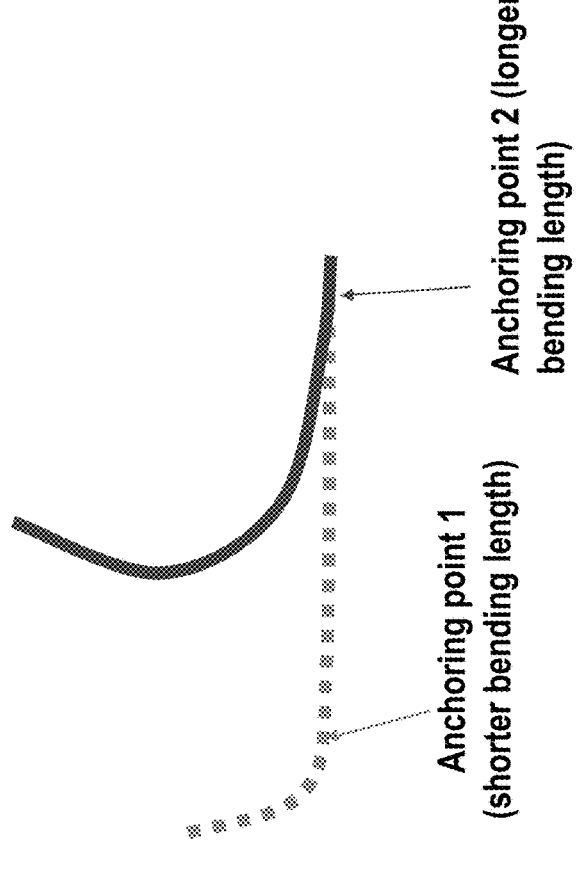
Anchoring point 2 (longer bending length)
Anchoring point 1 (shorter bending length)
FIG. 12A
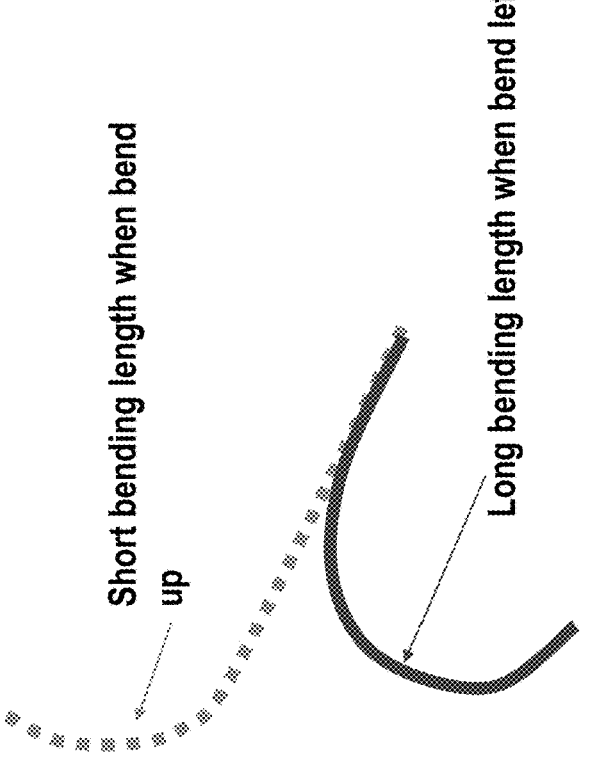
Short bending length when bend up
Long bending length when bend left

2000

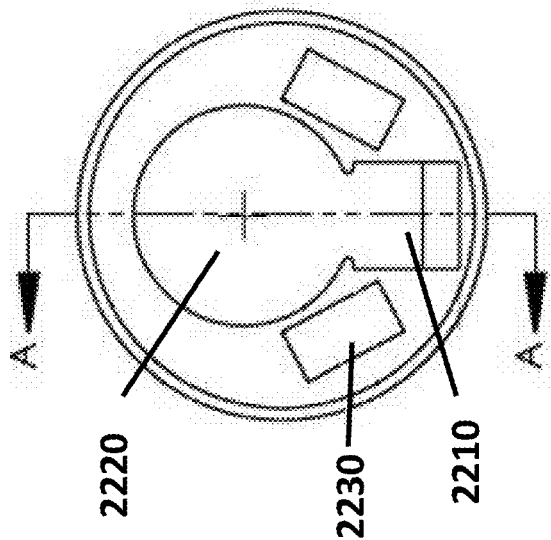
2220
2230
2210
FIG. 22
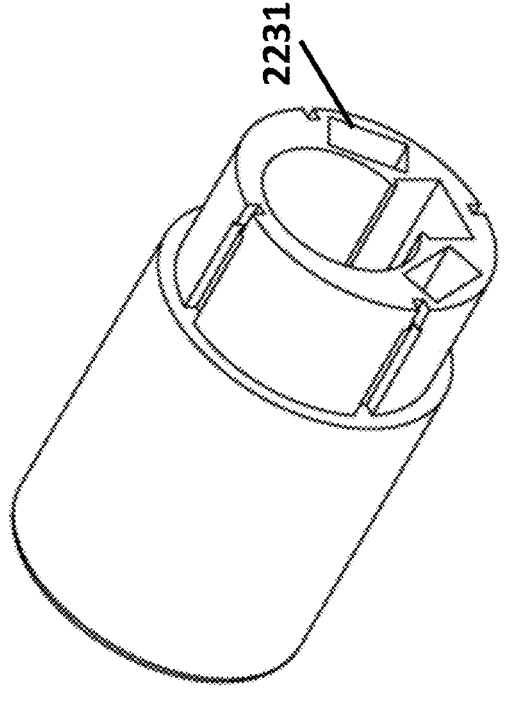
2231

SYSTEMS AND METHODS FOR CONFIGURABLE ENDOSCOPE BENDING SECTION

REFERENCE

This application is a continuation of International Application No. PCT/US2022/043997, filed on Sep. 19, 2022, which claims priority to U.S. Provisional Patent Application No. 63/250,263, filed on Sep. 30, 2021 which is entirely incorporated herein by reference.

BACKGROUND OF THE INVENTION

Endoscopy procedures use an endoscope to examine the interior of a hollow organ or cavity of the body. Unlike many other medical imaging techniques, endoscopes are inserted into the organ directly. Flexible endoscope that can deliver instinctive steering and control is useful in diagnosing and treating diseases that are accessible through any natural orifice in the body. Depending on the clinical indication, the endoscope may be designated as bronchoscope, ureteroscope, colonoscope, gastroscope, ENT scope, and various others. For example, flexible endoscopy has been used to inspect and treat disorders of the gastrointestinal (GI) tract without the need for creating an opening on the patient's body. The endoscope is introduced via the mouth or anus into the upper or lower GI tracts respectively. A miniature camera at the distal end captures images of the GI wall that help the clinician in their diagnosis of the GI diseases. Simple surgical procedures (like polypectomy and biopsy) can be performed by introducing a flexible tool via a working channel to reach the site of interest at the distal end.

In different medical procedures or applications, the bending requirement of the endoscope may be different. Even in the same procedure, there may be different bending requirements when the device is positioned at different locations of an anatomical structure.

SUMMARY OF THE INVENTION

Recognized herein is a need for a bending section of an endoscope with improved flexibility in the bending configuration. The present disclosure provides methods and apparatuses allowing for configurable bending section of a device. Additionally, the present disclosure provides low-cost, single-use articulatable endoscope for diagnosis and treatment in various applications such as bronchoscopy, urology, gynecology, arthroscopy, orthopedics, ENT, gastro-intestine endoscopy, neurosurgery, and various others. It should be noted that the provided endoscope systems can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

In some aspects of the present disclosure, an articulating flexible endoscope is provided. The endoscope comprises: a bending section connected to a distal tip portion of the articulating flexible endoscope at a first end, and connected to a shaft portion of the articulating flexible endoscope at a second end; a pull wire coupled to the distal tip portion at a first location and is configured for articulating the bending section; and a first tube for accommodating the pull wire, where a distal end of the first tube is coupled to a second location on the bending section or on the shaft portion, and where a proximal end of the first tube is coupled to a proximal portion of the articulating flexible endoscope. An effective bending section of the articulating flexible endoscope is adjusted by varying i) a length between the first location and the second location or ii) the second location. At least a portion of the articulating flexible endoscope is disposable.

In some embodiments, the distal tip portion comprises a structure to receive an imaging device, a position sensor, an illumination device. In some embodiments, the pull wires is placed inside of a lumen of the first tube and the pull wire has relative movement with respect to the first tube.

In some embodiments, the effective bending section is bent by the pull wire in a corresponding bending direction. In some embodiments, the endoscope further comprises a second tube coupled to the articulating flexible endoscope at a third location, and the first tube, the second tube and the pull wire are concentric. In some cases, the effective bending section comprises a first stage bending defined by the first location and the second location, and a second stage bending defined by the second location and the third location.

In some embodiments, the first tube has a length greater than the length of the corresponding portion of the articulating flexible endoscope. The first tube has a non-linear configuration or a spiral configuration. In some cases, the first tube is a hypotube and a wall thickness of the hypotube is selected based at least in part on a load transmission for transferring articulation force exerted on the bending section.

In some embodiments, the endoscope further comprises a guiding tube for guiding the pull wire to be aligned with the first tube at the proximal end of the first tube. In some cases, the guiding tube is a telescoping tube.

In some embodiments, the bending section comprises an inner tube having a plurality of tabs formed on an external surface of the inner tube. The plurality of tabs are configured to constrain the pull wire within a space. In some cases, the distal end of the first tube is coupled to the inner tube. Alternatively or additionally, the bending section comprises an outer tube having a plurality of tabs formed on an internal surface of the outer tube. In some embodiments, the entire articulating flexible endoscope is disposable or single-use.

In another aspect, a method is provided for a configurable bending section for an endoscope. The method comprises: providing a bending section, where the bending section is connected to a distal tip portion of the endoscope at a first end and a shaft portion of the endoscope at a second end; coupling a pull wire to the distal tip portion at a first location, where the pull wire is configured for articulating the bending section, where the pull wire is accommodated by a first tube; and coupling a distal end of the first tube to a second location on the bending section or on the shaft portion and coupling a proximal end of the first tube to a proximal portion of the endoscope. An effective bending section of the endoscope is adjusted by varying i) a length between the first location and the second location or ii) the second location.

In some embodiments, the distal tip portion comprises a structure to receive an imaging device, a position sensor, an illumination device. In some embodiments, the pull wires is placed inside of a lumen of the first tube and has a relative movement with respect to the first tube.

In some embodiments, the effective bending section is bent by the pull wire in a corresponding bending direction. In some embodiments, the method further comprises coupling a second tube to the endoscope at a third location, and the first tube, the second tube and the pull wire are concentric. In some cases, the effective bending section comprises a first stage bending defined by the first location and the second location, and a second stage bending defined by the second location and the third location.

In some embodiments, the first tube has a non-linear configuration or a spiral configuration. In some embodiments, the first tube is a hypotube and a wall thickness of the hypotube is selected based at least in part on a load transmission for transferring articulation force exerted on the bending section.

It should be noted that the provided modular endoscope components and various components of the device can be used in various minimally invasive surgical procedures, therapeutic or diagnostic procedures that involve various types of tissue including heart, bladder and lung tissue, and in other anatomical regions of a patient's body such as a digestive system, including but not limited to the esophagus, liver, stomach, colon, urinary tract, or a respiratory system, including but not limited to the bronchus, the lung, and various others.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 12A schematically illustrates different bending configurations for different bending directions.

FIG. 22 shows an example distal portion of a catheter with integrated imaging device and illumination device.

FIG. 26 shows an example of a guidewire with inflatable tip, in accordance with some embodiments of the invention.

DETAILED DESCRIPTION OF THE INVENTION

Figure 1:
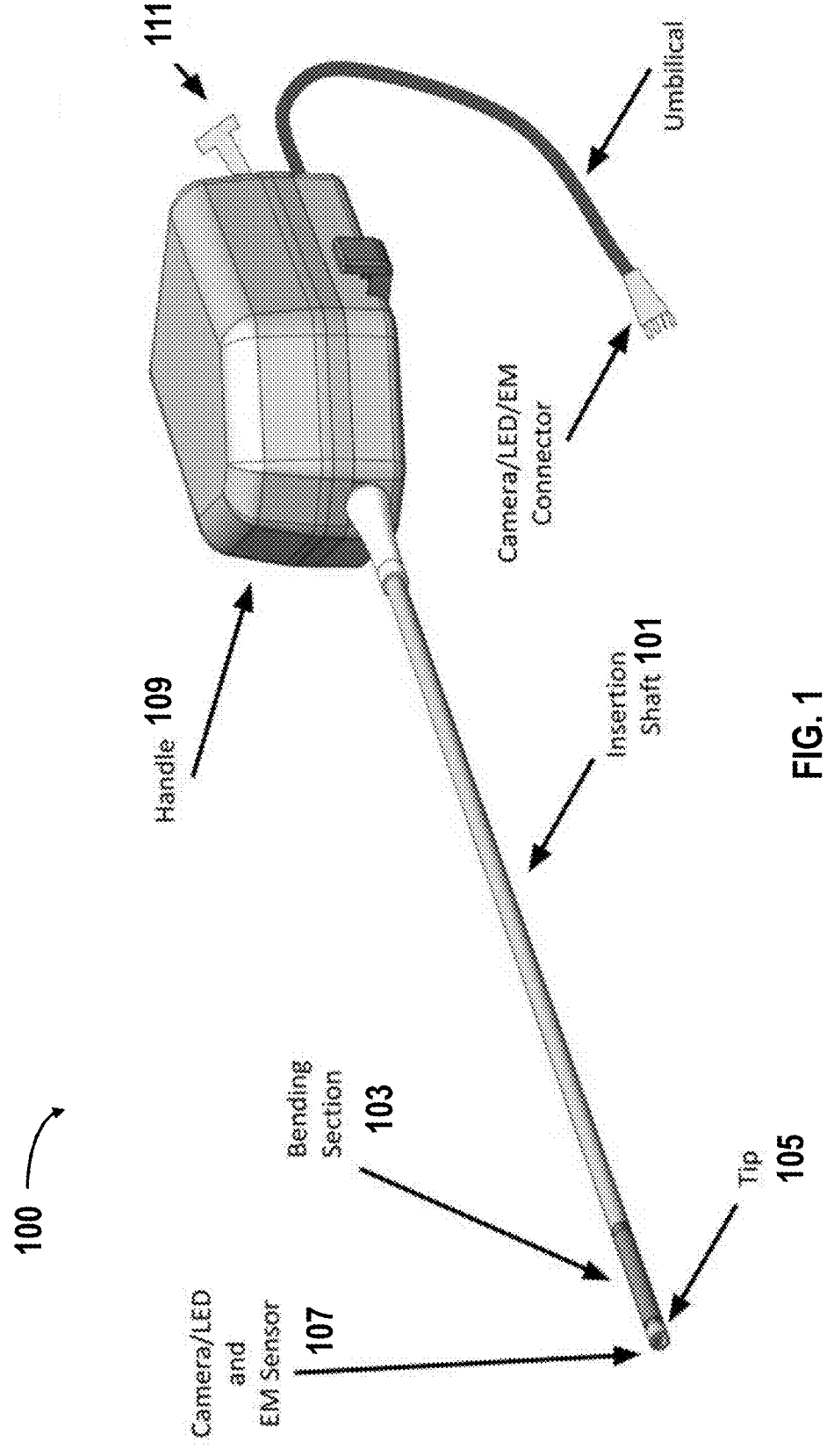
FIG. 1 illustrates an example of a flexible endoscope, in accordance with some embodiments of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

While exemplary embodiments will be primarily directed at a device or system for bronchoscopy, one of skill in the art will appreciate that this is not intended to be limiting, and the devices described herein may be used for other therapeutic or diagnostic procedures and in various anatomical regions of a patient's body. The provided device or system can be utilized in urology, gynecology, rhinology, otology, laryngoscopy, gastroenterology with the endoscopes, combined devices including endoscope and instruments, endoscopes with localization functions, one of skill in the art will appreciate that this is not intended to be limiting, and the devices described herein may be used for other therapeutic or diagnostic procedures and in other anatomical regions of a patient's body, such as such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat, and various others, in the forms of: NeuroendoScope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, SialendoScope, Orthopedic Endoscopes, and others, in combination with various tools or instruments.

The systems and apparatuses herein can be combined in one or more of many ways to provide improved diagnosis and therapy to a patient. Systems and apparatuses provided herein can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms distal and proximal may generally refer to locations referenced from the apparatus, and can be opposite of anatomical references. For example, a distal location of a primary shaft or catheter may correspond to a proximal location of an elongate member of the patient, and a proximal location of the primary sheath or catheter may correspond to a distal location of the elongate member of the patient.

Modular Flexible Endoscope

In an aspect of the invention, a flexible endoscope with improved performance at reduced cost is provided. FIG. 1 illustrates an example of a flexible endoscope 100, in accordance with some embodiments of the present disclosure. As shown in FIG. 1, the flexible endoscope 100 may comprise a handle portion 109 and a flexible elongate member to be inserted inside of a subject. In some embodiments, the flexible elongate member may comprise a shaft (e.g., insertion shaft 101), steerable tip (e.g., tip 105) and a steerable section (bending section 103). The endoscope 100 may also be referred to as steerable catheter assembly as described elsewhere herein. In some cases, the endoscope 100 may be a single-use robotic endoscope. In some cases, the entire catheter assembly may be disposable. In some cases, at least a portion of the catheter assembly may be disposable. In some cases, the entire endoscope may be released from an instrument driving mechanism and can be disposed of. In some embodiment, the endoscope may contain varying levels of stiffness along the shaft, as to improve functional operation.

The endoscope or steerable catheter assembly 100 may comprise a handle portion 109 that may include one or more components configured to process image data, provide power, or establish communication with other external devices. For instance, the handle portion may include a circuitry and communication elements that enables electrical communication between the steerable catheter assembly 100 and an instrument driving mechanism (not shown), and any other external system or devices. In another example, the handle portion 109 may comprise circuitry elements such as power sources for powering the electronics (e.g. camera, electromagnetic sensor and LED lights) of the endoscope.

The one or more components located at the handle may be optimized such that expensive and complicated components may be allocated to the robotic support system, a hand-held controller or an instrument driving mechanism, thereby reducing the cost and simplifying the design the disposable endoscope. In some cases, the handle portion may be in electrical communication with the instrument driving mechanism (e.g., FIG. 8, instrument driving mechanism 820) via an electrical interface (e.g., printed circuit board) so that image/video data and/or sensor data can be received by the communication module of the instrument driving mechanism and may be transmitted to other external devices/systems. In some cases, the electrical interface may establish electrical communication without cables or wires. For example, the interface may comprise pins soldered onto an electronics board such as a printed circuit board (PCB). For instance, receptacle connector (e.g., the female connector) is provided on the instrument driving mechanism as the mating interface. This may beneficially allow the endoscope to be quickly plugged into the instrument driving mechanism or robotic support without utilizing extra cables. Such type of electrical interface may also serve as a mechanical interface such that when the handle portion is plugged into the instrument driving mechanism, both mechanical and electrical coupling is established. Alternatively or in addition to, the instrument driving mechanism may provide a mechanical interface only. The handle portion may be in electrical communication with a modular wireless communication device or any other user device (e.g., portable/hand-held device or controller) for transmitting sensor data and/or receiving control signals.

In some cases, the handle portion 109 may comprise one or more mechanical control modules such as luer 111 for interfacing the irrigation system/aspiration system. In some cases, the handle portion may include lever/knob for articulation control. Alternatively, the articulation control may be located at a separate controller attached to the handle portion via the instrument driving mechanism.

The endoscope may be attached to a robotic support system or a hand-held controller via the instrument driving mechanism. The instrument driving mechanism may be provided by any suitable controller device (e.g., hand-held controller) that may or may not include a robotic system. The instrument driving mechanism may provide mechanical and electrical interface to the steerable catheter assembly 100. The mechanical interface may allow the steerable catheter assembly 100 to be releasably coupled to the instrument driving mechanism. For instance, a handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool. Details about the instrument driving mechanism are described later herein.

In the illustrated example, the distal tip of the catheter or endoscope shaft is configured to be articulated/bent in two or more degrees of freedom to provide a desired camera view or control the direction of the endoscope. As illustrated in the example, imaging device (e.g., camera), position sensors (e.g., electromagnetic sensor) 107 is located at the tip of the catheter or endoscope shaft 105. For example, line of sight of the camera may be controlled by controlling the articulation of the bending section 103. In some instances, the angle or orientation of the camera may be adjustable such that the line of sight can be adjusted without or in addition to articulating the distal tip of the catheter or endoscope shaft. For example, the camera may be oriented at an angle (e.g., tilt) with respect to the axial direction of the tip of the endoscope with aid of an optical component.

The distal tip 105 may be a rigid component that allows for positioning sensors such as electromagnetic (EM) sensors, imaging devices (e.g., camera) and other electronic components (e.g., LED light source) being embedded at the distal tip.

In real-time EM tracking, the EM sensor 107 comprising of one or more sensor coils embedded in one or more locations and orientations in the medical instrument (e.g., tip of the endoscopic tool) measures the variation in the EM field created by one or more static EM field generators. The one or more static EM field generators may be positioned at a location close to a patient. The location information detected by the EM sensors is stored as EM data. The EM field generator (or transmitter) may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. For example, the EM field generator may be positioned close to the patient torso during procedure to locate the EM sensor position in 3D space or may locate the EM sensor position and orientation in 5D or 6D space. This may provide a visual guide to an operator when driving the bronchoscope towards the target site. Details about the tip design and the plurality of components embedded at the tip are described later herein.

The endoscope may have a unique design in the shaft component. In some cases, the insertion shaft of the endoscope may comprise a single tube that incorporates a series of cuts (e.g., reliefs, slits, etc.) along its length to allow for improved flexibility as well as a desirable stiffness. Details about the shaft design is described later herein.

The bending section 103 may be designed to allow for bending in two or more degrees of freedom (e.g., articulation). A greater bending degree such as 180 and 270 degrees (or other articulation parameters for clinical indications) can be achieved by the unique structure of the bending section. In some cases, the bending section may be fabricated separately as a modular component and assembled to the insertion shaft 101. In some cases, the bending section may further incorporate minimalist features thereby reducing cost and increasing reliability. For example, the bending section may incorporate a cut pattern that beneficially allows for a greater degree of tube deflection to achieve a desired tip displacement relative to the insertion shaft. In some embodiments, the distal portion of the catheter assembly may comprise two or more bending sections connected in series. The modular design of the bending section may beneficially allow for adding or removing a bending section from the catheter assembly.

Figure 2:
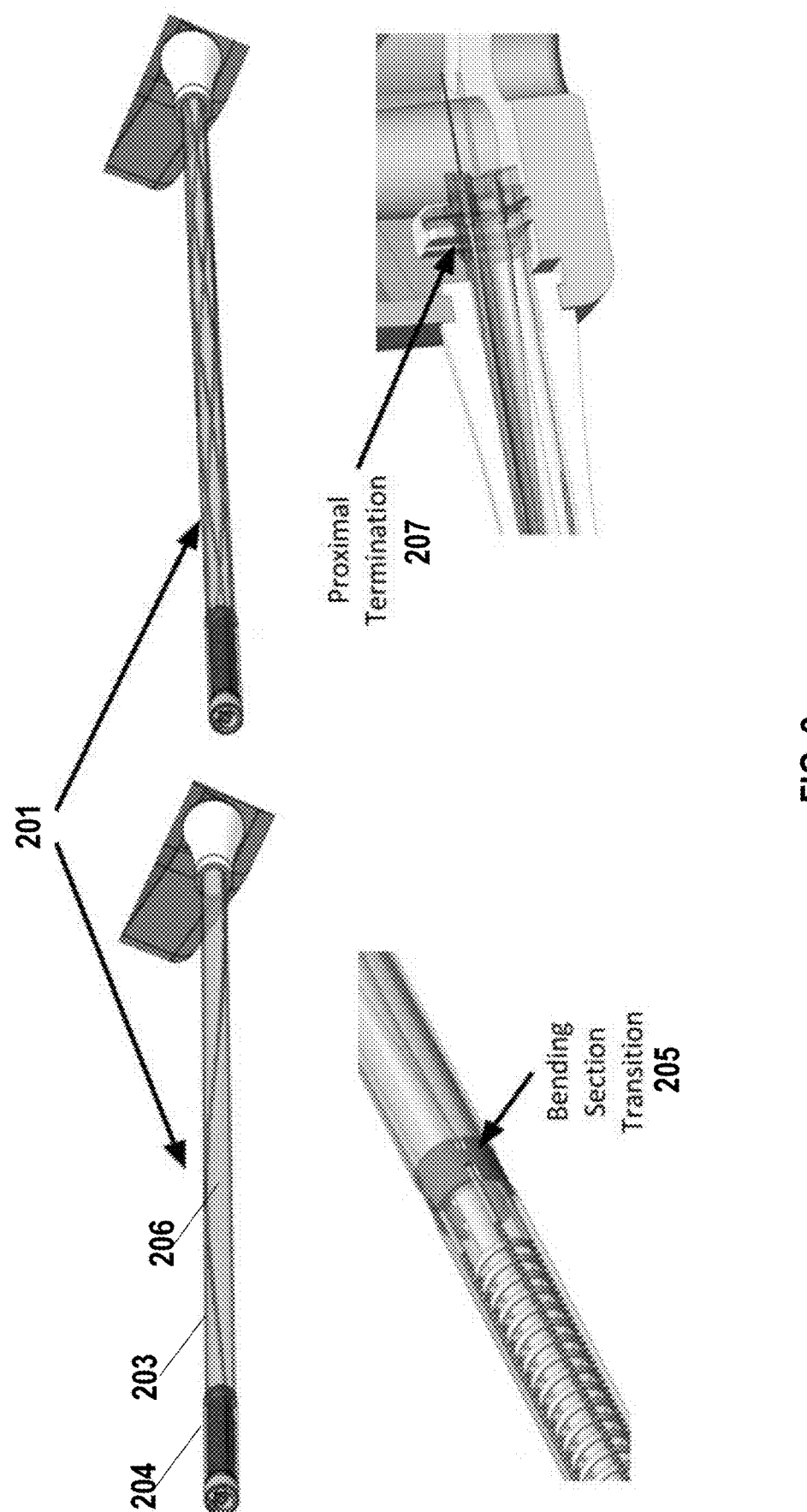
FIG. 2 shows an example of an endoscope with an articulation force transmission mechanism, in accordance with some embodiments of the invention.

In some embodiments, the endoscope may comprise an articulation force transmission mechanics to ensure that the endoscope is stable and delivers instinctive bending section responsiveness. FIG. 2 shows an example of an endoscope with an articulation force transmission mechanism 201, in accordance with some embodiments of the invention. The articulation force transmission mechanism 201 may include a plurality of load transmission tubes that are located inside the bore of the insertion shaft/tube 206. In some cases, at least one, two, three, four, five or more load transmission tubes may be included to reduce the axial compression/extension (strain) of the insertion tube 203 during articulation of the bending section 204. The load transmission tubes may transmit at least a portion of the articulation load applied to the bending section and/or the shaft back to the handle (e.g., via actuator or motors that drive one or more articulating pull wires).

The shaft portion 206 may comprise one or more load transmission tubes for accommodating the one or more pull wires. The transmission tubes resolve the articulation loads allowing for an improved stability of the insertion shaft 206. The plurality of load transmission tubes 201 may reside within the lumen of the shaft tube (i.e., tube bore) and be configured to transfer articulation or distal end effector reaction forces from the bending section to the handle portion. The end effector may be an active end effector such as a tissue grabber, ablation electrode (e.g., tissue grabber 302 in FIG. 3A). Alternatively, the end effector may be passive such as a distal tip that is embedded with a camera (e.g., distal tip 304 in FIG. 3A). The load transmission tubes are configured to transfer the bending section articulation reaction forces back to the handle portion thereby reducing the articulation forces that would have been applied to the insertion shaft tube. Such a design may be beneficial in preventing these forces from being resolved through the insertion shaft tube in the form of undesired and indeterministic shaft compression or torsion thereby providing a stable shaft. The transmission modality described herein may ensure that the insertion shaft tube experiences minimal axial compressive or extension forces, thereby remaining stable during the articulation of the bending section.

In preferred embodiments of the load transmission mechanism, the plurality of load transmission tubes 201 may be longer than the length of the insertion shaft tube 203 in a free state. The length of the plurality of load transmission tubes 201 may be determined such that when the load transmission tubes are under axial compression, they are still longer than the length of the insertion shaft tube 203 thereby preventing loads caused by path length changes created by shaft bending from transferring through the insertion shaft tube. In some cases, the free length of the transmission tubes may be chosen such that when the transmission tubes are assembled in the load transmission mechanism, the axial stiffness of the transmission tubes under compression is greater than the axial stiffness of the insertion shaft tube. For example, the length of the load transmission tubes may be at least 0.01%, 0.1%, 0.2%, 0.3%, 1%, 5%, 10% longer than the length of the insertion shaft. The length of the load transmission tubes may be determined based at least in part on the dimension of the inner diameter of the shaft. For example, the load transmission tubes may have a spiral configuration that provides sufficient stiffness to bear/transmit the load.

The load transmission tubes may have a dimension and configuration that can accommodate a displacement within the shaft tube. For example, when the insertion shaft tube 203 is bent such as due to being subjected to a tortuous anatomy, the insertion shaft tube may cause displacement of components housed within the bore of the insertion shaft tube. In this case, the extra length of the load transmission tubes may beneficially accommodate the displacement within the insertion shaft tube bore while improving stability of the shaft. Compared to existing techniques that may utilize coil pipes and service loop within the handle portion, the modular design and assembly of the load transmission tubes may beneficially reduce the cost without compromising the performance of the shaft. Compared to other existing techniques that has the pull wires built into the shaft (shown in FIG. 6), the provided load transmission mechanism may beneficially transmit load from the bending section to the handle without compressing the shaft thereby improving the shaft stability.

The plurality of load transmission tubes may be anchored at the proximal end 207 and distal end 205 of the insertion shaft tube 203. As described above, because the load transmission tubes are longer than the length of the insertion shaft tube, the load transmission tubes may have a non-linear/straight configuration within the bore of the insertion shaft tube allowing for the flexibility to adjust to the displacement caused by bending. For example, the one or more load transmission tubes may have a non-straight (e.g. spiraled) configuration allowing for movement within the main lumen of the endoscope to account for geometry changes to the length of the shaft when the endoscope is subjected to tortuous configurations while being placed in the anatomy. Such load transmission mechanism may beneficially serve as a natural spring to counteract to the motion from the outer insertion shaft.

In some embodiments, the one or more load transmission tubes may enclose one or more pull wires. The articulation of the endoscope may be controlled by applying force to the distal end of the endoscope via one or multiple pull wires. The one or more pull wires may be attached to the distal end of the endoscope. In the case of multiple pull wires, pulling one wire at a time may change the orientation of the distal tip to pitch up, down, left, right or any direction needed. In some cases, the pull wires may be anchored at the distal tip or end effector of the endoscope, running through the bending section, and entering the handle where they are coupled to a driving component (e.g., pulley). In some cases, the endoscope may comprise more two or more bending sections, and the pull wires may be anchored at the end of each respective bending section. This handle pulley may interact with an output shaft from the robotic system.

Figure 3A:
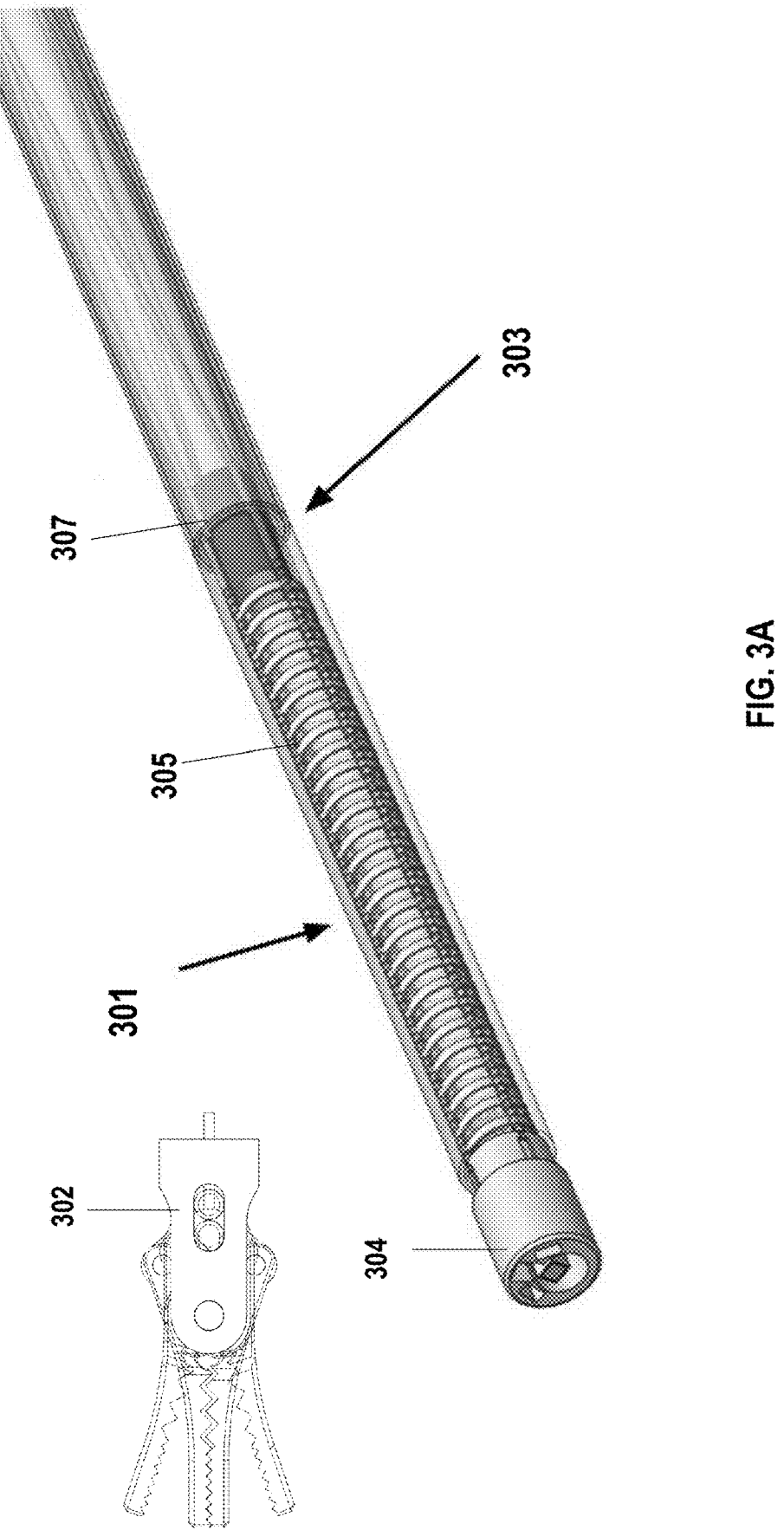
FIG. 3A and FIG. 3B show examples of one or more pull wires assembled with one or more load transmission tubes at a bending section.
Figure 3B:
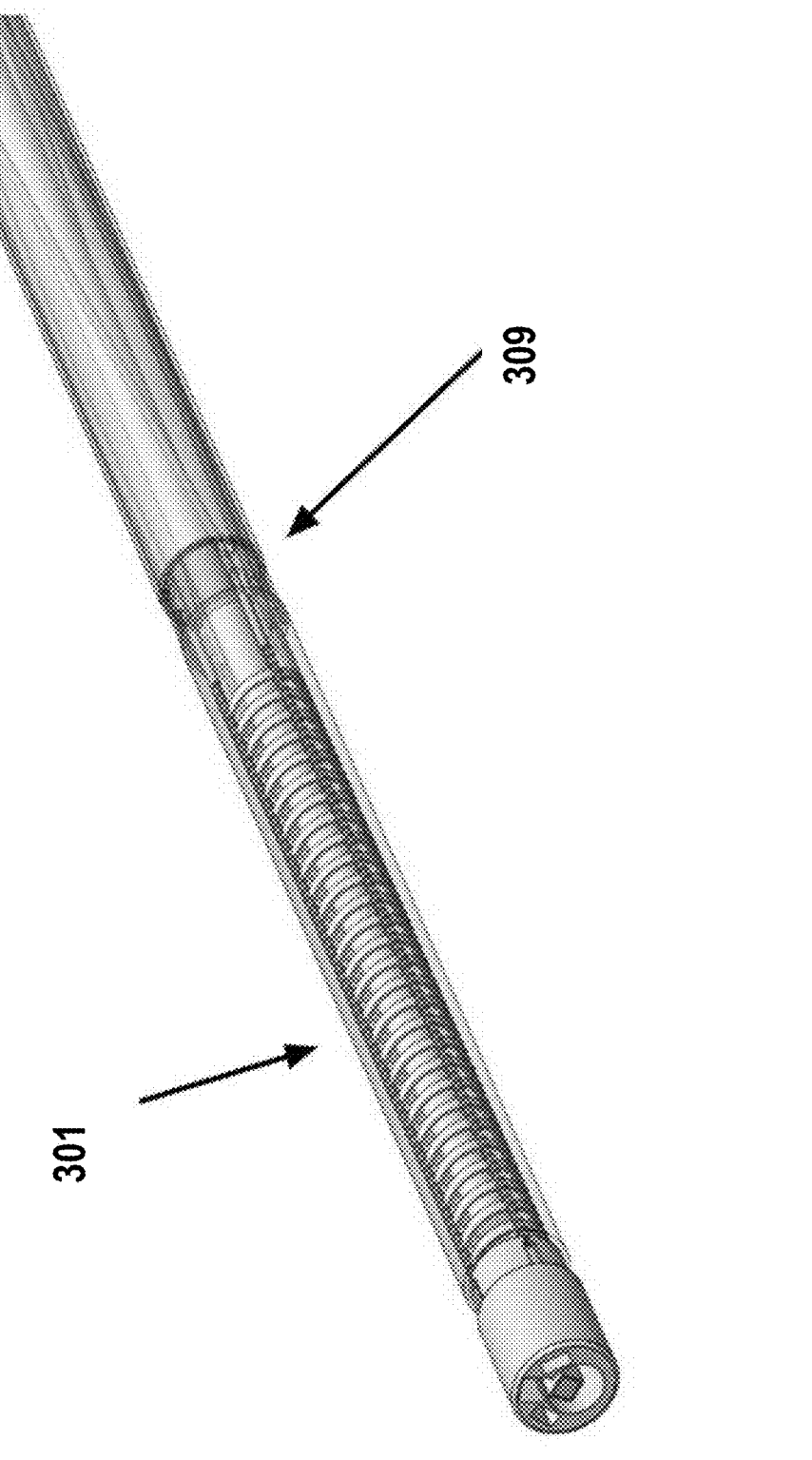

In some embodiments, the one or more pull wires may be located within the one or more load transmission tubes or running through the inside of the transmission tubes. FIG. 3A and FIG. 3B show examples of one or more pull wires 305 assembled with the load transmission tubes 307 at the bending section 301. As shown in FIG. 3A, the bending section 301 may be composed of stainless steel ribbon. The bending section may be formed of other suitable structures or materials to achieve pre-determined bending stiffness while maintaining desired axial and torsional stiffness with low articulation force. For example, the bending section may comprise braid structures for torsional stability. In the illustrated example, a plurality of pull wires 305 may run through or be placed inside of the lumen of the load transmission tubes 307 and the bending section, terminated at the distal portion of the endoscope. For instance, the pull wire may be anchored to the distal tip 304 or the end effector 302 (e.g., tissue grabber).

For example, a driving mechanism (e.g., actuators, motors) may be engaged with the pull wires to articulate the bending section. The one or more load transmission tubes may be configured to transmit at least a portion of the articulation loads (e.g., compression) from the bending section back to the handle or motors, for example, by placing the one or more pull wires inside the one or more load transmission tubes, respectively. There may be relative motion between the pull wire and the corresponding load transmission tube during articulation. The one or more load transmission tubes may transmit at least a portion of the articulation load applied to the bending section and/or the shaft back to the handle (e.g., motors that drive one or more articulating pull wires). This may beneficially reduce at least a portion of the articulation force applied to the bending section and/or the insertion shaft thereby improving stability of the insertion shaft.

The endoscope may comprise a bending section transition 303 that is located at the junction interface of the bending section and the shaft. The bending section transition 303 may comprise structures that may enable efficient and convenient assembly of the endoscope. For example, the bending section transition 303 may include mechanical components such as snaps/clips to anchor the load transmission tubes (e.g., hypotubes) to the cutout features on the insertion shaft. FIG. 3B shows another example of the bending section transition 309. In the illustrated example, the load transmission tubes may be anchored to the interface between the insertion shaft and the bending section by welding to the transition ring structure of the bending section transition 309. This may beneficially reduce the abrupt stiffness change between the shaft portion and the bending section thereby preventing kinking.

Figure 3C:
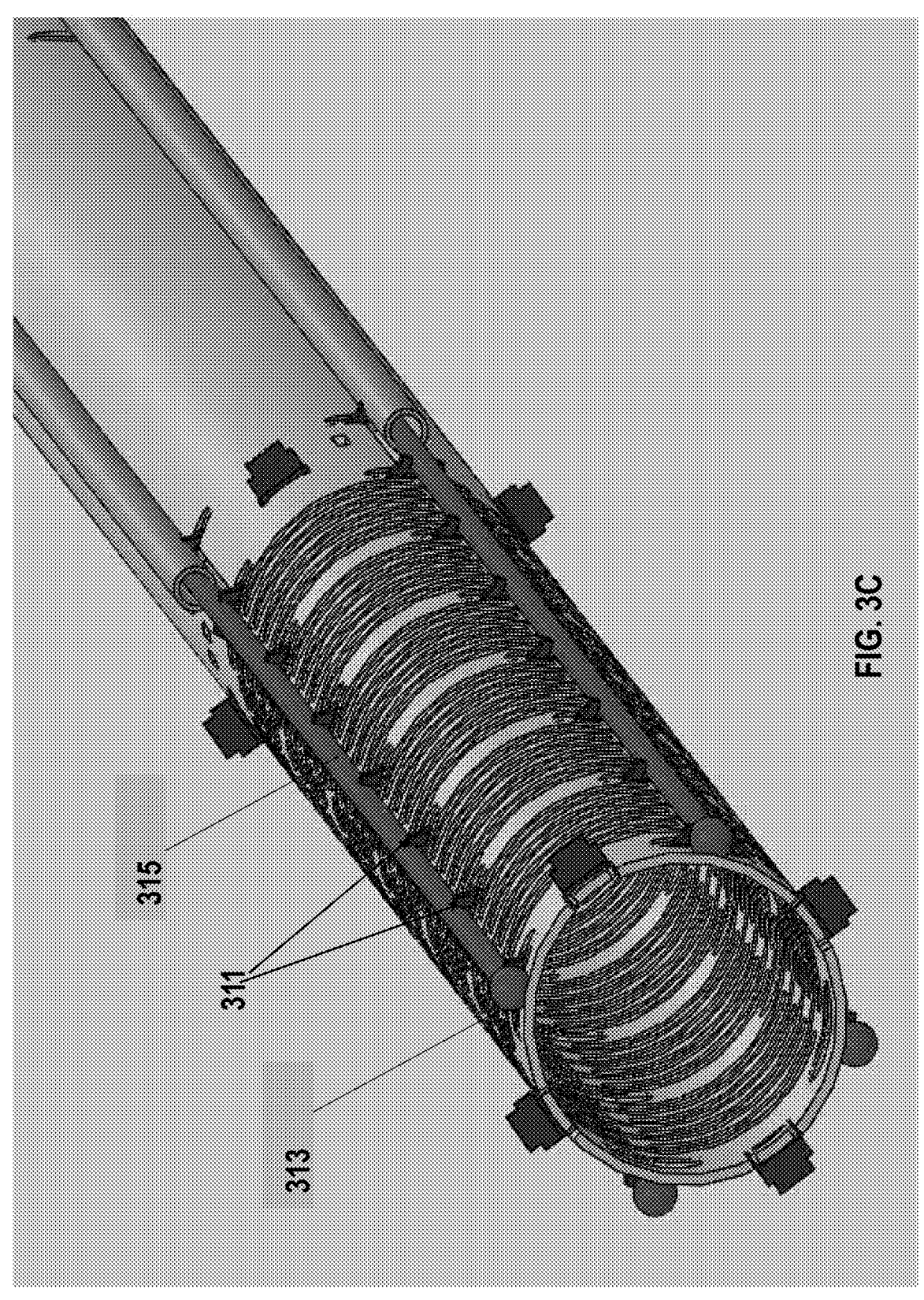
FIG. 3C and FIG. 3D shows an example of arranging a pull wire in the bending section.
Figure 3D:
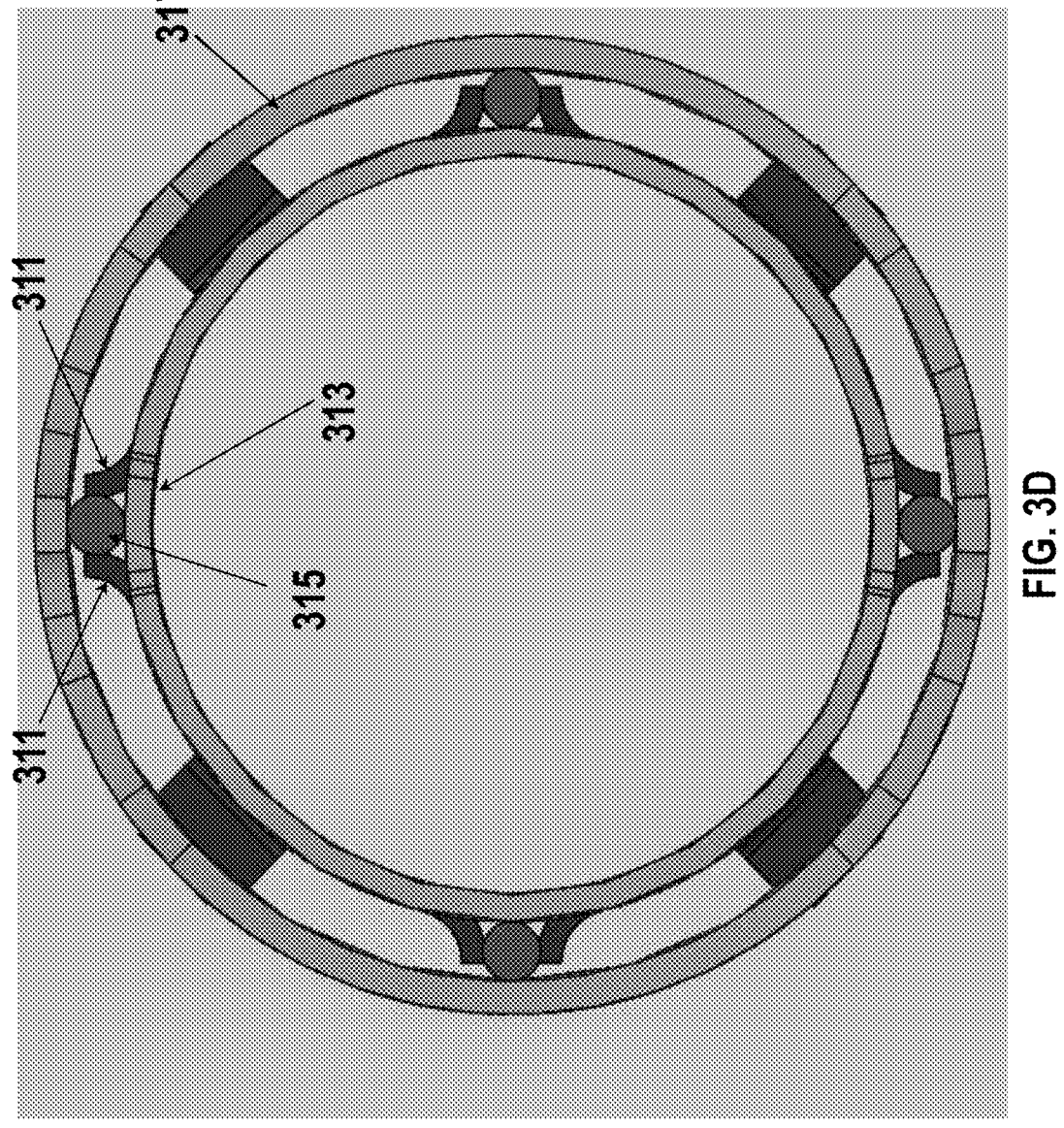

FIG. 3C and FIG. 3D shows an example of arranging the pull wire 315 in the bending section. In some embodiments, the bending section may comprise at least two concentric tubes including an inner tubing 313 and an outer tubing 317. In some case, the inner tubing 313 and an outer tubing 317 may have complementary mechanical properties. For instance, the inner tube 313 may have the necessary torsional stiffness while the outer tube 317 may provide sufficient compressive stiffness. The inner tubing 313 and the outer tubing 317 may or may not rotate relative to each other.

The cut out on the inner tubing 313 of the bending section may comprise a series of tabs 311. In some cases, the series of tabs 311 may form a linearity array on the external surface of the inner tubing 313. As illustrated in FIG. 3D, the array of tabs may form a chute for a pull wire 315 to be confined in the space between two opposing tabs 311, the inner tube surface 313, and an outer tube 317. The tabs may form a pull wire moving chute and may be used as anchoring points for pull wires or the hypotubes.

In some embodiments, an array of tabs may correspond to one pull wire. In some cases, the array of tabs may have an optimal pattern. In some cases, the number of tabs and spacing of tabs may be varied to enable the corresponding pull wire(s) moving on a predefined path (e.g., linear or curve), during pulling and pushing of the pull wire(s). The variation in the pattern of the tabs beneficially allows a design of in-plane bending and non-in-plane bending. For example, a helical shape of the bending section may be formed by arranging the tabs in a helical pattern.

The tabs 311 may be formed on an external surface of the inner tube 313. Alternatively, tabs 311 may be formed on an internal surface of the outer tube 317. In some cases, the tabs 311 may be formed on both the inner tube 313 and the outer tube 317.

Figure 4:
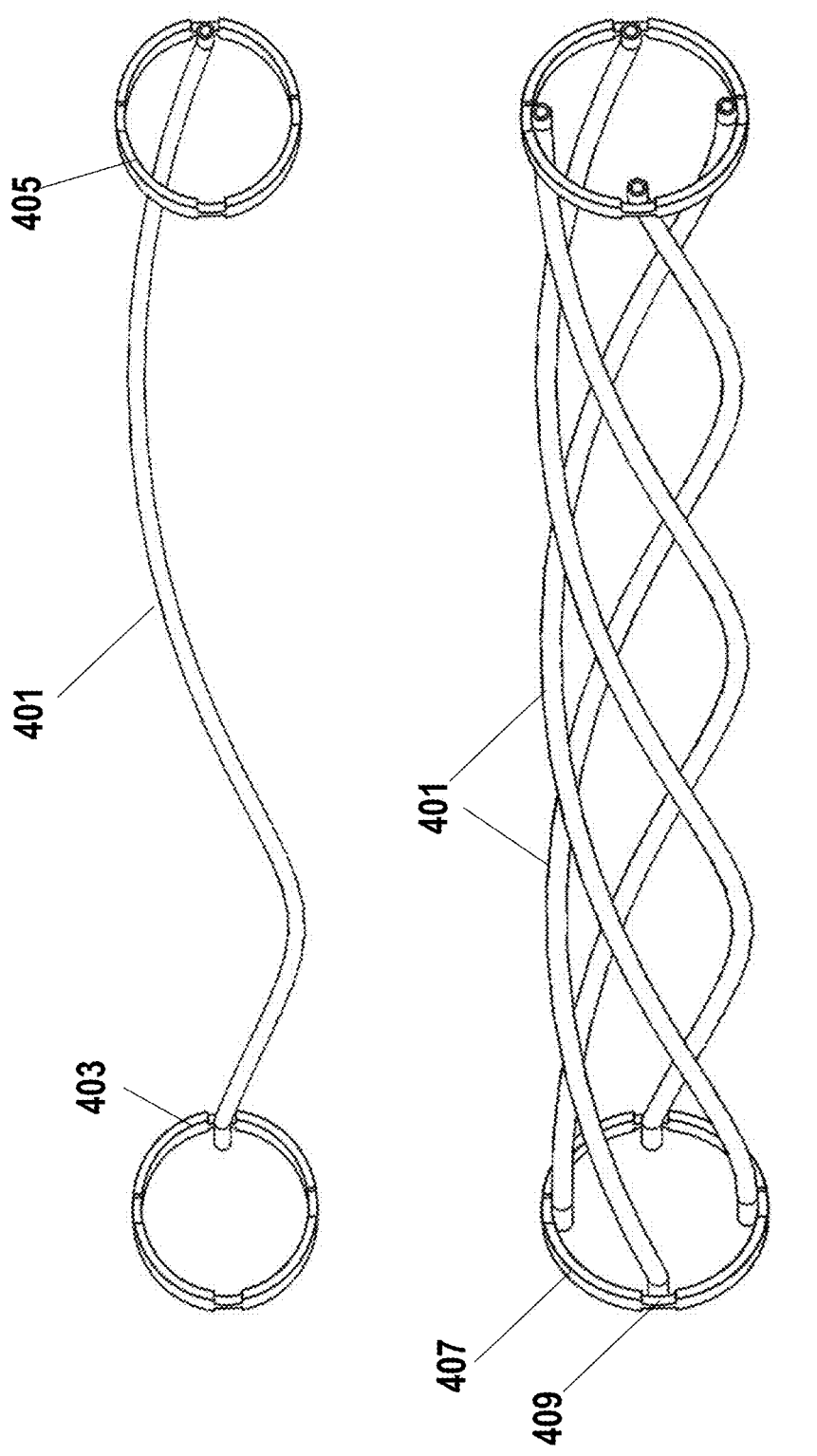
FIG. 4 shows an example of a load transmission tube terminated at a distal shaft region and proximal shaft region.

FIG. 4 shows an example of a load transmission tube 401 terminated at a distal shaft region 403 and proximal shaft region 405. As described above, the load transmission tube may have a non-linear/non-straight configuration within the bore of the insertion tube thereby allowing for the flexibility to adjust to the displacement caused by bending. The load transmission mechanism may comprise one or more load transmission tubes as shown in the example. Such load transmission mechanism may beneficially serve as a natural spring to counteract to the motion from the outer insertion shaft without requiring extra service loop at the handle portion. In the illustrated example, the end portion of the load transmission tube may be fixedly connected (e.g., welded or soldered to) the bending section transition 407. The bending section transition 407 may comprise a coupling structures 409 (e.g., snap) for easy assembling to the insertion shaft.

In some cases, the one or more load transmission tubes may be composed of materials such as metallic tubing or metallic wound coil pipe. The geometry and/or materials of the load transmission tubes may be selected/determined to provide desired axial and bending stiffness. For example, the material may be metallic materials such as stainless steel or nitinol, stiff polymers such as PEEK, glass or carbon filled PEEK, Ultem, Polysulfone and other suitable materials. In addition, the transmission tube can be chosen to be composed of multiple constructions (such as a wound coil pipe attached to metallic tubing). In some cases, the one or more load transmission tubes may have an inner diameter greater than the outer diameter of the pull wire to allow for relative movement (e.g., translational and/or rotational movement) between the load transmission tubes and the pull wire. In some cases, the transmission tube may have non-constant diameters along the length. For example, an inner diameter, an outer diameter, or the combination of inner and outer diameter may be variable along the length direction. The wall thickness of the one or more load transmission tubes may be determined based on a function of the load transmission needed to transfer the articulation loads of the bending section.

Figure 5:
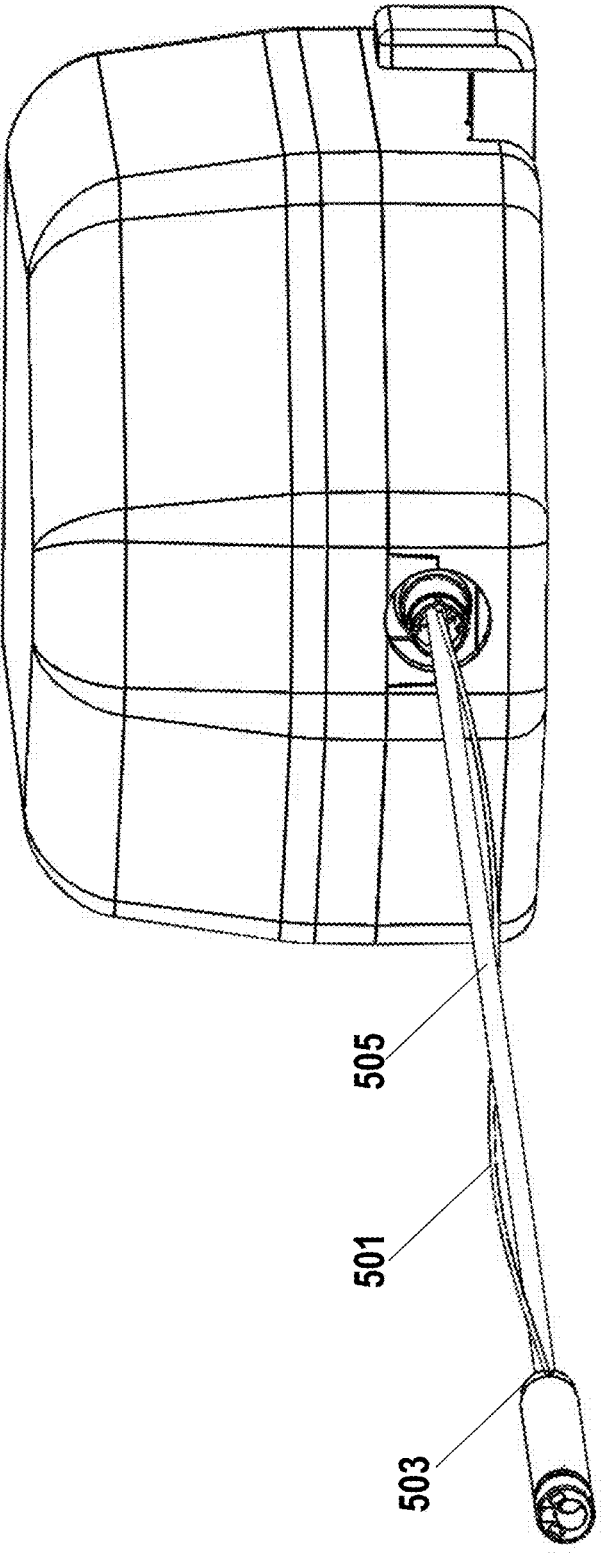
FIG. 5 shows an example of a load transmission tube terminated at a distal shaft region and proximal shaft region.

FIG. 5 shows an example of a load transmission tube 501 terminated at a distal shaft region 503 and proximal shaft region. As described elsewhere herein, the load transmission tube 501 may be located within the lumen of the insertion shaft (not shown) and external to the working channel 505.

Figure 6:
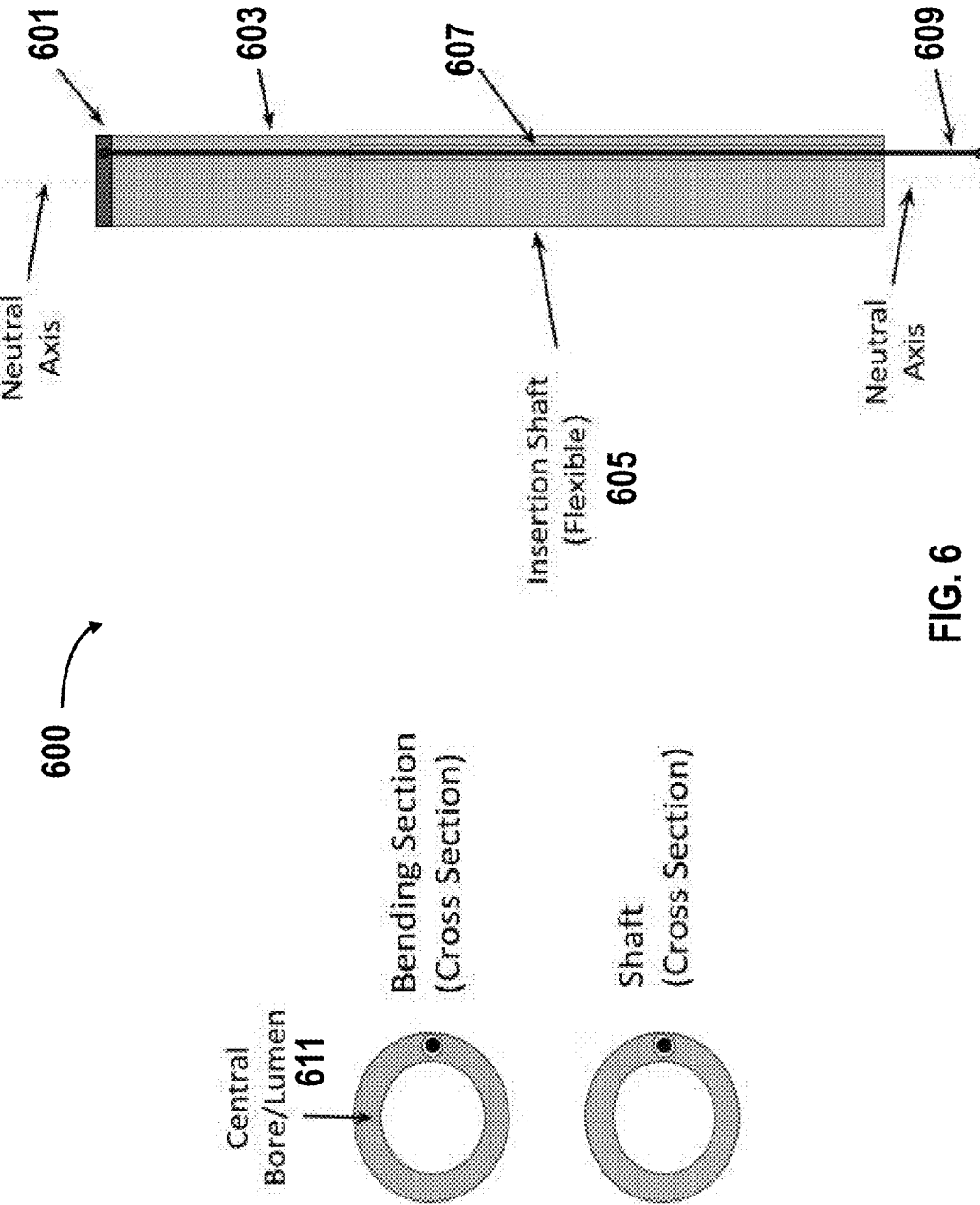
FIG. 6 shows an example of an existing steerable catheter architecture.

FIG. 6 shows an example of an existing steerable catheter architecture 600. In the existing catheter design, without load transmission tubes, the one or more pull wires 609 are usually running through conduits 607 that are built into the walls of the insertion shaft 605 and bending section 603. The catheter shaft may have a central bore/lumen 611 coaxial with the neutral axis. As shown in the cross-section view, the shaft wall or the bending section wall may have a built-in structure (e.g., lumens, conduits) to let the pull wires pass through. In such case, the shaft may bear the articulation load which may result in an unstable shaft.

Figure 7:
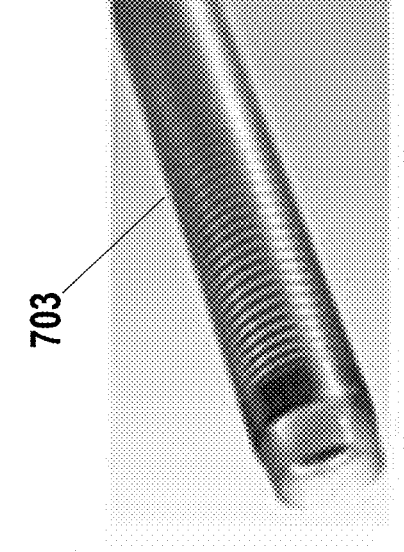
FIG. 7 shows an example of a design for an insertion shaft.
Figure 7:
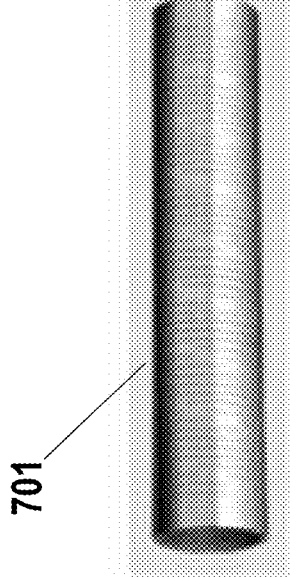

FIG. 7 shows examples of the design for the insertion shaft. As described above, the insertion shaft of the endoscope may consist of a single tube with an integrally formed structure to vary a stiffness of the shaft portion. For example, the tube may have a series of cuts (or reliefs, slits, etc.) formed along the length. The cuts in the tube may have varied profile/pattern 701, 703 and density along the length to generate a variable bending stiffness from the distal region to the proximal region. This may beneficially allow for controlling the bending stiffness parameters by controlling the cuts in the insertion shaft. In some case, the tube may be the bending section.

Endoscope with Configurable Bending Section

In an aspect of the present disclosure, a flexible endoscope with improved bending performance is provided. The bending section of the endoscope may be configurable. For example, the bending section may be configurable by changing at least a bending length, a bending location and/or a bending radius. In some embodiments, the configurable bending section may be adjusted by changing an effective bending length, or location of a bending section. In some embodiments, the bending section may be further adjusted with respect to a given bending direction.

In some embodiments, the configurable bending section may be adjusted by varying an anchoring location of one or more transmission tubes. In some cases, the configurable bending section may also be referred to as the effective bending section which is based on the anchoring point of the pull wire and the anchoring point of the hypotube (i.e. transmission tubes). In some cases, the one or more hypotubes can be the same as the load transmission tubes as described above. Instead of or in addition to fixing a distal end of the one or more tubes to the bending section transition similar to the load transmission tubes, the distal anchoring point of the one or more tubes may be located at various positions along the flexible elongate member thereby varying a configuration of the bending section. For instance, by varying the distal location of a hypotube attached to the inner lumen, the shaft or the tube (e.g., laser cut tubes) of the bending section, different bending configurations may be achieved.

Figure 8:
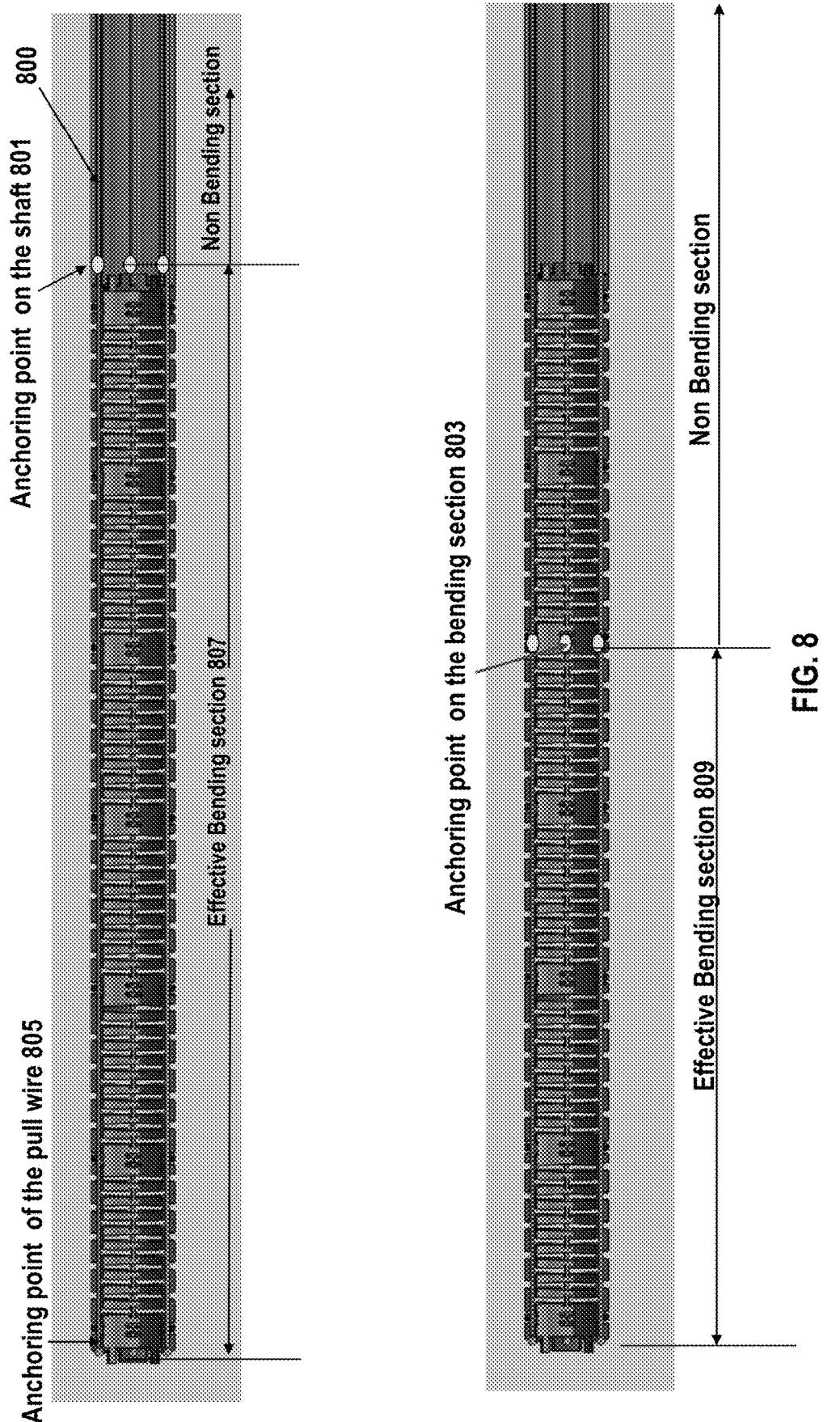
FIG. 8 shows an example of a tube with the distal end affixed to different anchoring points along the length of a flexible elongate member.

FIG. 8 shows an example of a tube 800 with the distal end affixed to different anchoring points 801, 803 along the length of a flexible elongate member. Similar to the load transmission tubes, a pull wire may run through or be placed inside of the lumen of the tube 800 and may be slidable relative to the tube.

In some cases, the tube 800 may provide support to the flexible elongate instrument as well as being substantially flexible (e.g., able to bend in various directions and orientations). In particular, the tube 800 may provide axial support and transmit at least a portion of the articulation load applied to the bending section and/or the shaft back to the proximal handle thereby affecting a bending performance. The tube 800 may have axial stiffness but flexible in bending. This may affect the bending property of the catheter. For instance, when a compressible force or load is applied to the tube 800 such as using the pull wire to apply force to the anchoring point of the pull wire, the tube 800 may transmit the axial load to the proximal handle thereby affecting or altering the effective bending length, bending location and/or bend radius of at least a portion of the catheter.

In some cases, the bending section 807, 809 of the flexible elongate member may be configurable by adjusting an anchoring location of the tube 801 and/or the anchoring location of the pull wire 805. One or more tubes 800 may be utilized to vary or change the bending configuration, bending length, and/or bend radius of a portion or certain portion of the catheter by changing the positioning or placement of the anchoring point 801, 803 of the tubes 800 along the flexible elongate member.

In the illustrated example, the anchoring point 801 of the one or more tubes 800 may be located at the shaft portion resulting in the corresponding bending section 807 from the anchoring point of the pull wire 805 to the anchoring point 801 of the tube. By moving the anchoring point 803 to a position at the bending section (e.g., moving closer to the tip), the effective bending section 809 is shortened compared to the effective bending section 807. The shorter effective bending section may also correspond to a greater bend radius. The portion from the anchoring point 801 of the tubes 800 to the proximal end may be non-bending section which may be substantially flexible or pliable and passively following the movement of the bending section. By varying the location of the anchoring point of the one or more tubes 800 in various portions of the flexible elongate member or catheter may substantially affect the bend radius, bend length, and/or bend location of at least a portion of the catheter as pull wires are operated to articulate or steer the catheter.

Figure 9:
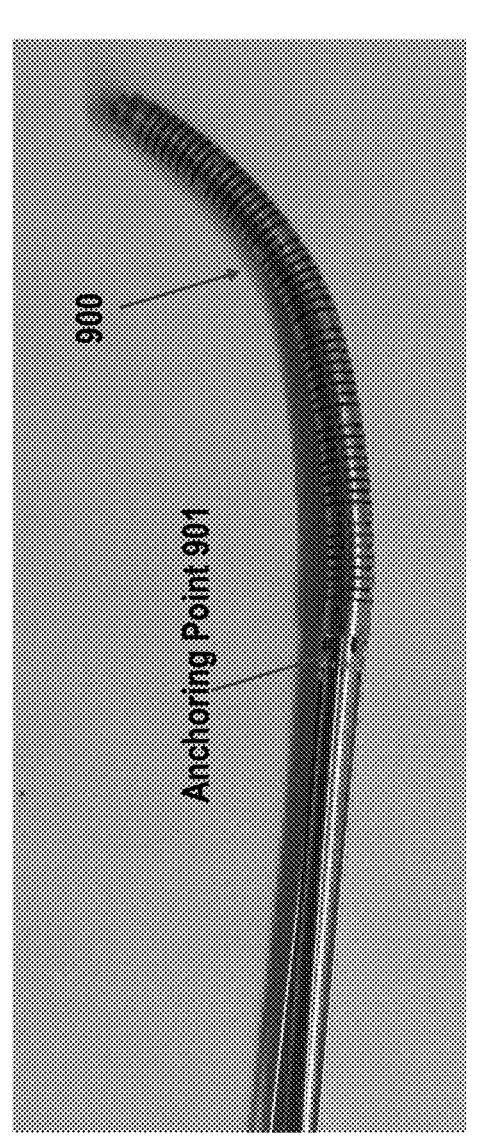
FIG. 9 shows examples of different bending radii and/or bending lengths are achieved by varying the anchoring location of the hypotube.
Figure 9:
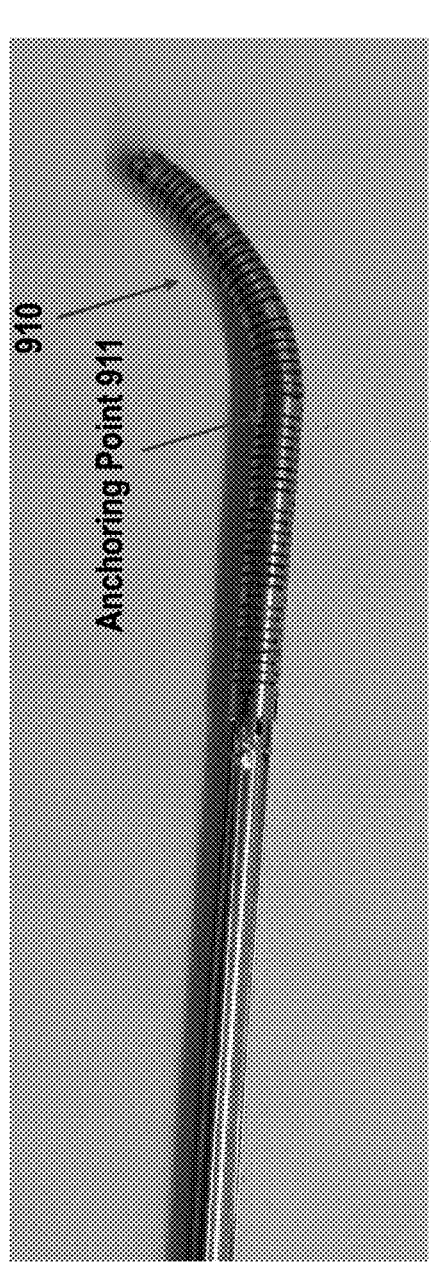

A distal end of the one or more tubes 800 may be fixed to the catheter at various locations. The distal end of the one or more tubes may or may not be removably fixed to the catheter. The coupling of the distal end of the tubes may or may not be fixed. For example, the distal end of the tube may be soldered, welded, crimped, or interlocked in any suitable manner to a specific location on a bending section (e.g., anchoring point 803), on a shaft portion (e.g., anchoring point 801) or any other portion of the flexible elongate member. The distal end of the tubes may be secured to the flexible elongate member in any suitable manner. For example, the distal portion of one or more tubes may be fused, soldered or welded to the material of the shaft, or the laser cut tube of the bending section. Alternatively, the distal end of the tubes may be coupled to or decoupled from the bending section without tools. FIG. 9 shows examples of different bending radii and/or bending lengths are achieved by varying the anchoring location of the hypotube. In a first example, by coupling the hypotube to a first anchoring point 901, a first bending radius (greater radius) 900 is achieved.

In a second example, by coupling the hypotube to a second anchoring point 911 (closer to the tip), a second bending radius (smaller radius) 910 is achieved.

Figure 10:
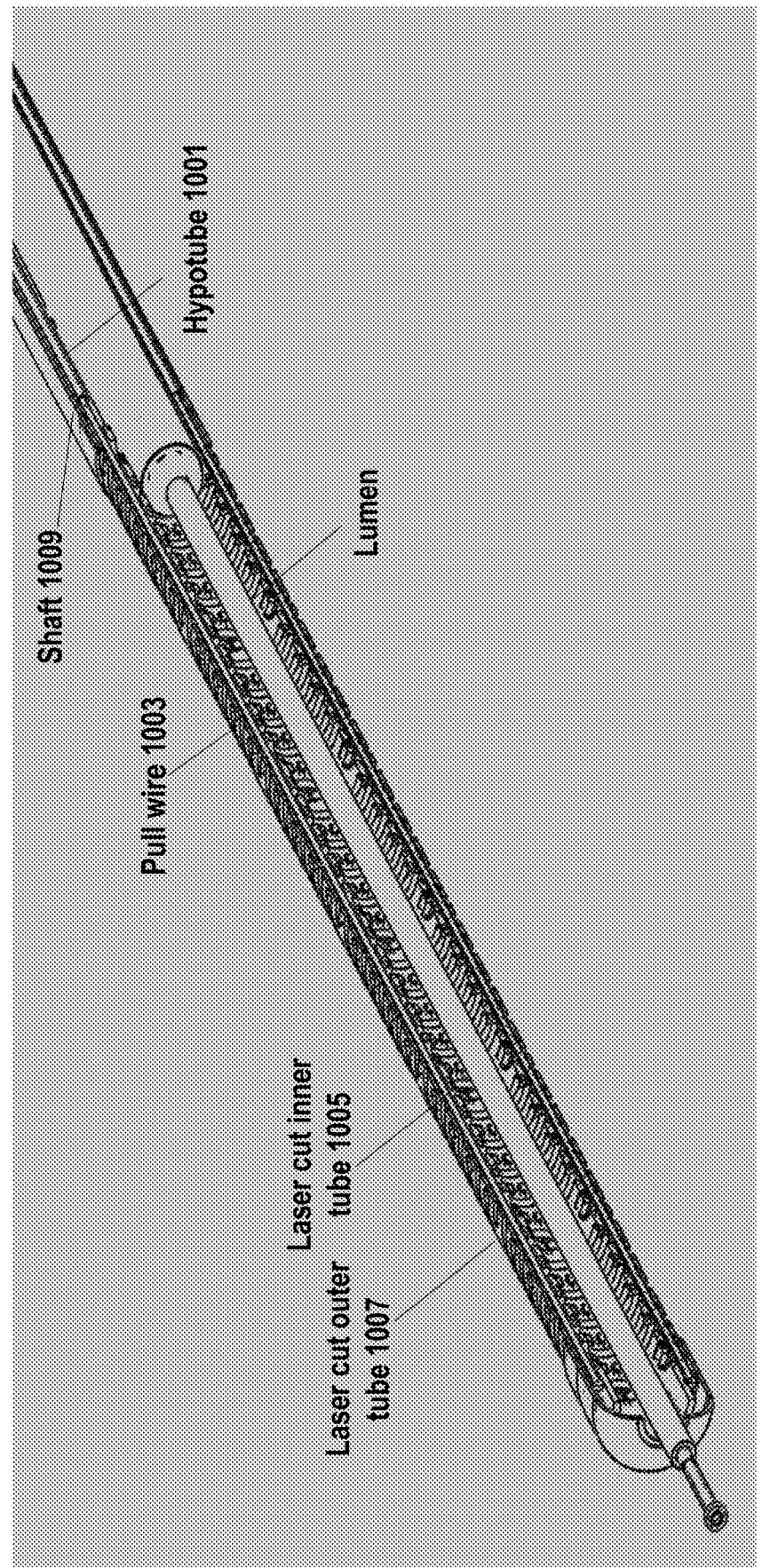
FIG. 10 shows an example of using hypotube for providing configurable bending section.

The geometry and/or materials of the one or more tubes may be selected/determined to provide desired axial and bending stiffness. For example, the one or more tubes may be stainless steel hypodermic tubing (hypotube). FIG. 10 shows an example of using hypotube 1001 for providing configurable bending section. The hypotube 1001 may be made from of stainless steel, a high durometer plastic or other suitable material. For instance, the material may be metallic materials such as stainless steel or nitinol, stiff polymers such as PEEK, glass or carbon filled PEEK, Ultem, Polysulfone and other suitable materials. In some cases, the one or more hypotubes 1001 may have a coating to reduce fiction (e.g., when it moves relative to the pull wire or a guide wire).

In some cases, the hypotube 1001 may have an inner diameter greater than the outer diameter of the pull wire 1003 to allow for relative movement (e.g., translational and/or rotational movement) between the hypotube 1001 and the pull wire 1003. The wall thickness of the one or more hypotubes 1001 may be determined based on a function of the load transmission needed to transfer the articulation loads of the bending section.

In the example shown in FIG. 10, the bending section may have an inner laser cut tubing 1005 and an outer laser cut tubing 1007, and the hypotube 1001 may be placed between the inner laser cut tubing 1005 and the outer laser cut tubing 1007 when its distal anchoring point is located at the bending section. In some cases, the inner laser cut tubing 1005 and an outer laser cut tubing 1007 can be the same as the inner tubing and outer tubing as described in FIG. 3C and FIG. 3D. For instance, the distal end of the hypotube 1001 may be fixed to the inner laser cut tubing 1005 at an anchoring point. When the anchoring point is located at the shaft portion 1009, the distal end may be fixed to the shaft or a bending section transition feature as described above. It should be noted that the two laser cut tubes in the bending section are for illustration purpose only and the bending section may have various other designs (e.g., a single laser cut tubing) as described elsewhere herein.

Operation of one or more pull wires 1003 may steer or articulate any of the location, section, portion, or region of the catheter. The anchoring point of the pull wire along with the anchoring point of the hypotube may provide a configurable bending section with various bend radii, bending length or bending location for the articulated portion of the catheter. The one or more pull wires 1003 can be the same as the pull wires as described elsewhere herein. For example, the pull wire may be connected to a distal portion of the catheter. As described later herein, the one or more pull wires 1003 may be attached to an integrally formed structure of the distal portion. For example, the integrally formed structure may comprise grooves that are molded with the distal tip. The grooves may have a dimension or size that match the dimension of the distal end of the pull wire such that the pull wire can be conveniently crimped at the distal portion of the catheter. This may advantageously improve the assembly efficiency, reduce the cost thereby allowing for a single-use device. In some instances, the pull wires may be rigidly affixed to the grooves at the distal end such that the distal end of the pull wire may not be permitted to move relative to the distal portion of the catheter.

In some embodiments, the device may comprise a plurality of pull wires and hypotubes for articulating the tip portion in various bending directions. For example, by pulling one pull wire at a time, the orientation of the distal tip may be steered to pitch up, down, left, right, and by pulling a combination of multiple wires concurrently, any direction may be achieved. In the case of multiple pull wires or multiple hypotubes are employed, the distal anchoring points of the multiple hypotubes may or may not be at the same location along the longitudinal axial/length direction.

In some embodiments, the location of the anchoring points may be varied to control the radius of curvature of a bending section of the catheter as the catheter is articulated or steered. In some embodiments, the plurality of tubes may be anchored at substantially the same points or regions of the flexible elongate member along the longitudinal axial direction. In some embodiments, the tubes may be anchored at substantially different points or regions of the flexible elongate member to affect the bending radius of various portions of the flexible elongate member and/or various directions of steering or bending. For example, the bending length along the 'up' direction may be different from the bending length along the 'left' direction. This beneficially allows for the flexibility to configure the bending configuration with respect to a selected direction and/or to achieve complex bending configurations.

Figure 11:
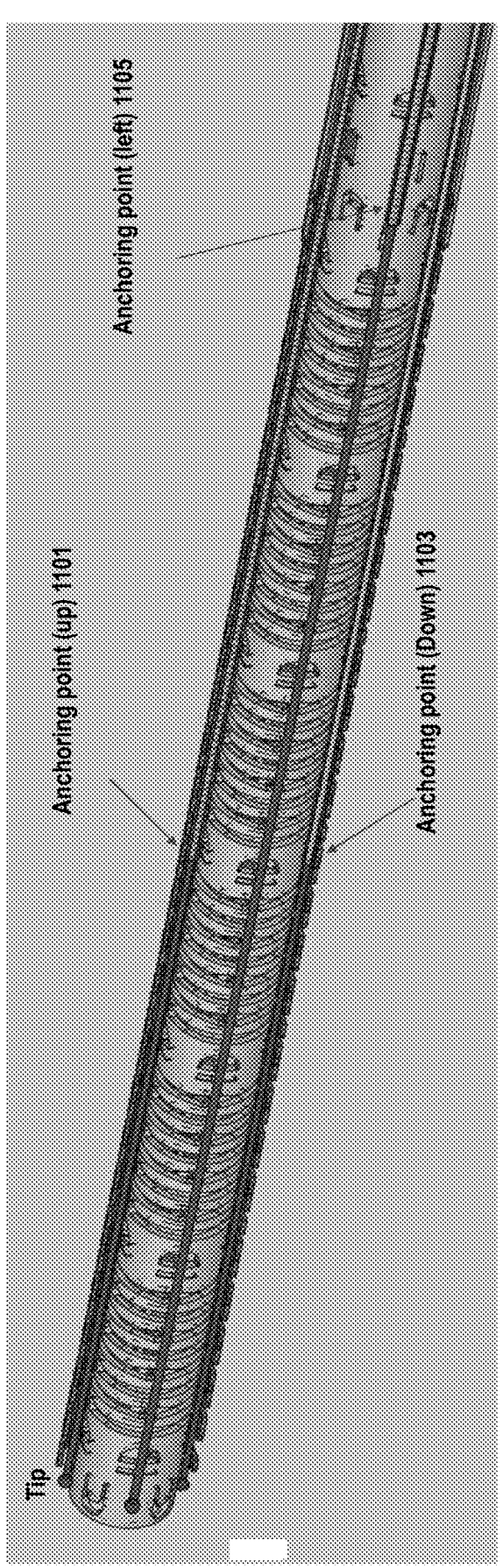
FIG. 11 shows an example of configuring a bending length/radii for a given direction.

FIG. 11 shows an example of configuring the bending length/radii for a given bending direction. The anchoring point 1101 of the tube corresponding to the 'up' direction and the anchoring point 1103 of the tube corresponding to the 'down' direction may be located at the bending section whereas the anchoring point 1105 of the tube corresponding to the 'left' direction may be located at the shaft resulting in a longer bending length compared to those of the 'up' or 'down' direction.

Figure 12B:
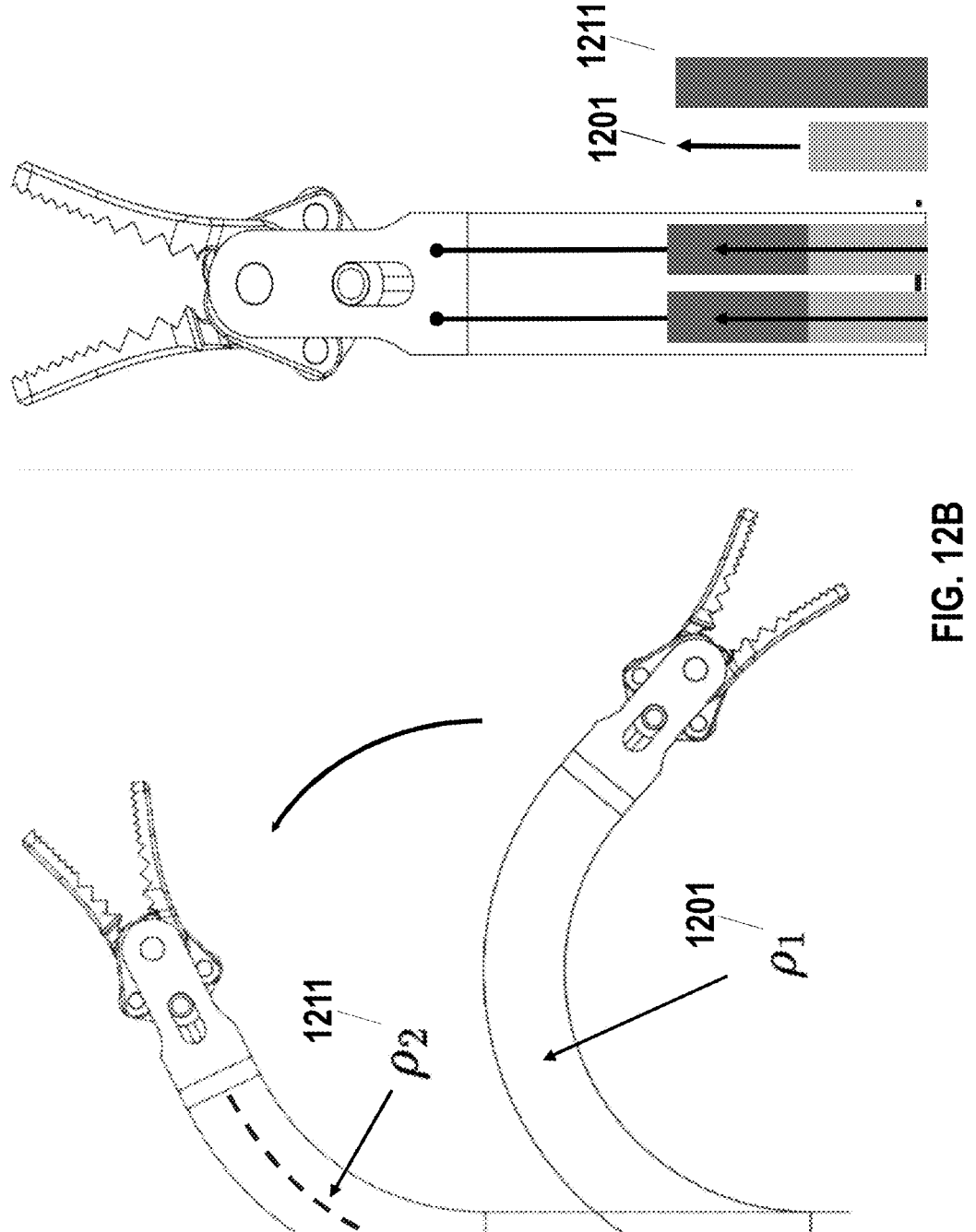
FIG. 12B shows an example of the different bending radii can be achieved by varying the location of anchoring point.

As illustrated in FIG. 12A, when the pull wire length between the tip and anchoring point ('up' direction) 1101 is shorter, the effective bending length of the bending section is shorter resulting in a greater bend radius. Similarly, when the pull wire length between the tip and anchoring point ('left' direction) 1105 is longer, the effective bending length is longer resulting in a smaller bend radius. FIG. 12B shows another example of the different bending radii can be achieved by varying the anchoring point. In a first configuration 1201 with the anchoring point further away from the tip (i.e., longer effective bending section), a smaller bending radius 1201 is achieved. In a second configuration 1211 with the anchoring point closer to the tip (i.e., shorter effective bending section), a greater bending radius 1211 is achieved.

Figure 13:
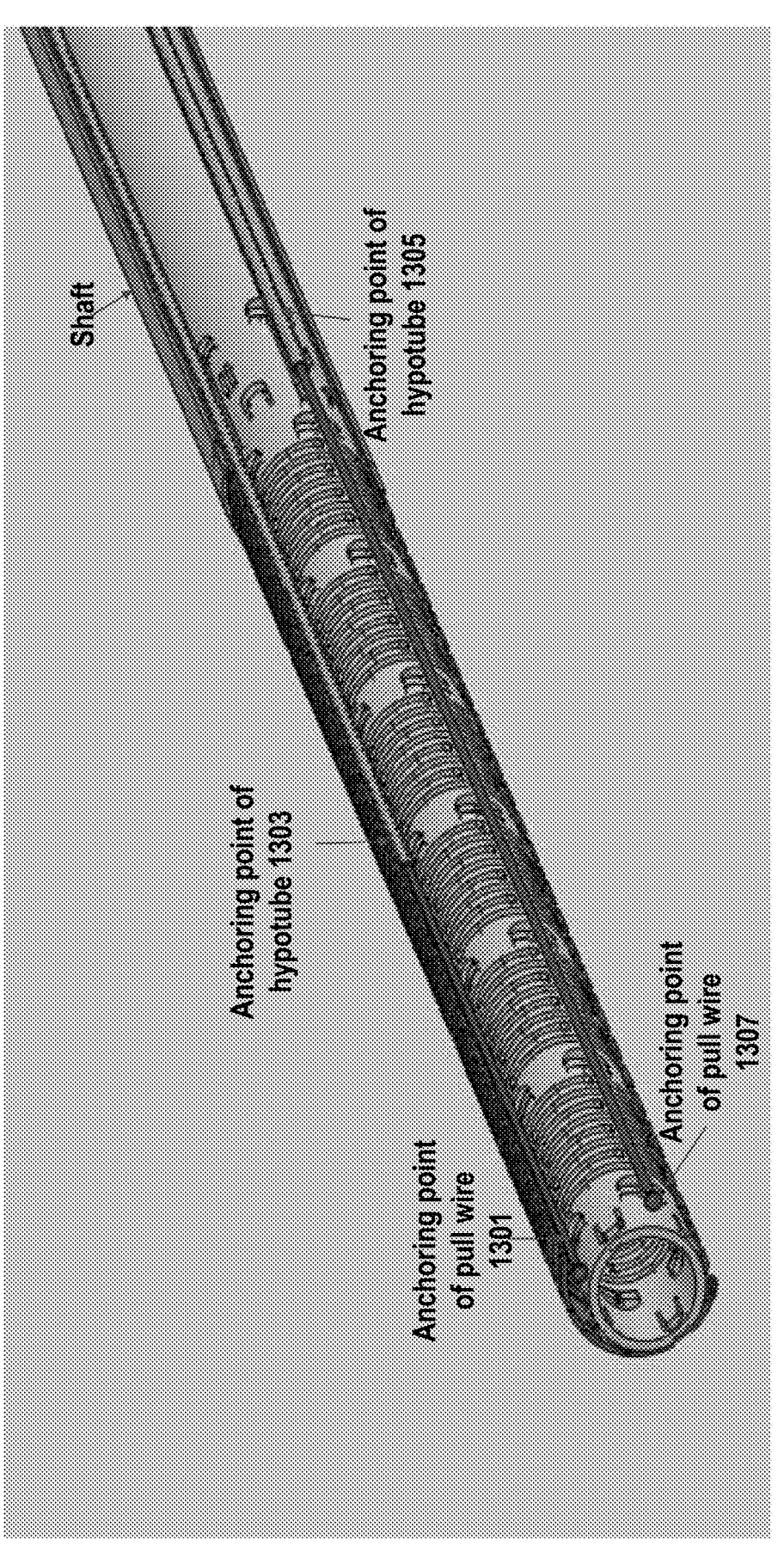
FIG. 13 shows an example of adjusting an effective bending length by varying the anchoring point of the pull wire and the anchoring point of the hypotube.

FIG. 13 shows another example of adjusting the effective bending length by varying the anchoring point of the pull wire 1301 and the anchoring point of the hypotube 1303. As shown in the example, the distal end of the pull wire corresponding to a first direction may be anchored to the bending section (e.g., laser cut tube) at an anchoring point 1301 such as by soldering or welding. The distal end of the hypotube aligned with the pull wire may be anchored to the bending section (e.g., laser cut tube) at another anchoring point 1303 such as by soldering or welding. The length between the first anchoring point 1301 and the second anchoring point 1303 may determine the effective bending length with respect to the first direction. The distal end of a second hypotube corresponding to a second direction may be anchored to the bending section at an anchoring point 1305 and the length between the anchoring point 1305 and the anchoring point of the corresponding pull wire 1307 may be greater than the length corresponding to the first direction resulting in a longer effective bending length.

In some embodiments, the pull wire and hypotube may be on a neutral plan to reduce the impact on the bending shape.

For example, the pull wires and hypotubes corresponding to the up/down direction may be on the neutral plane and may be located closer to a wall of the flexible elongate member than the central axis of the flexible elongate member. The axially stiff property of the hypotube may beneficially shift the neutral axis from the catheter cross-sectional centroid to be aligned with the pull wire for articulation consistency.

The anchoring points can be placed at various position for various combination of curvatures or a composite bending configuration. This may beneficially allow a user, operator or surgeon to easily manipulate the catheter to conform, adopt, or match the various shape or curvatures of the internal pathways of a patient while the catheter is being advanced and steered to reach various tissue structures or target sites inside a patient. In some embodiments, the catheter may comprise two or more hypotubes corresponding to a bending direction such that the flexible elongate member may be steered, articulated, or deflected into various complex shapes or curvatures (e.g., "S" curved shapes or any other composite curves, etc.).

Figure 14:
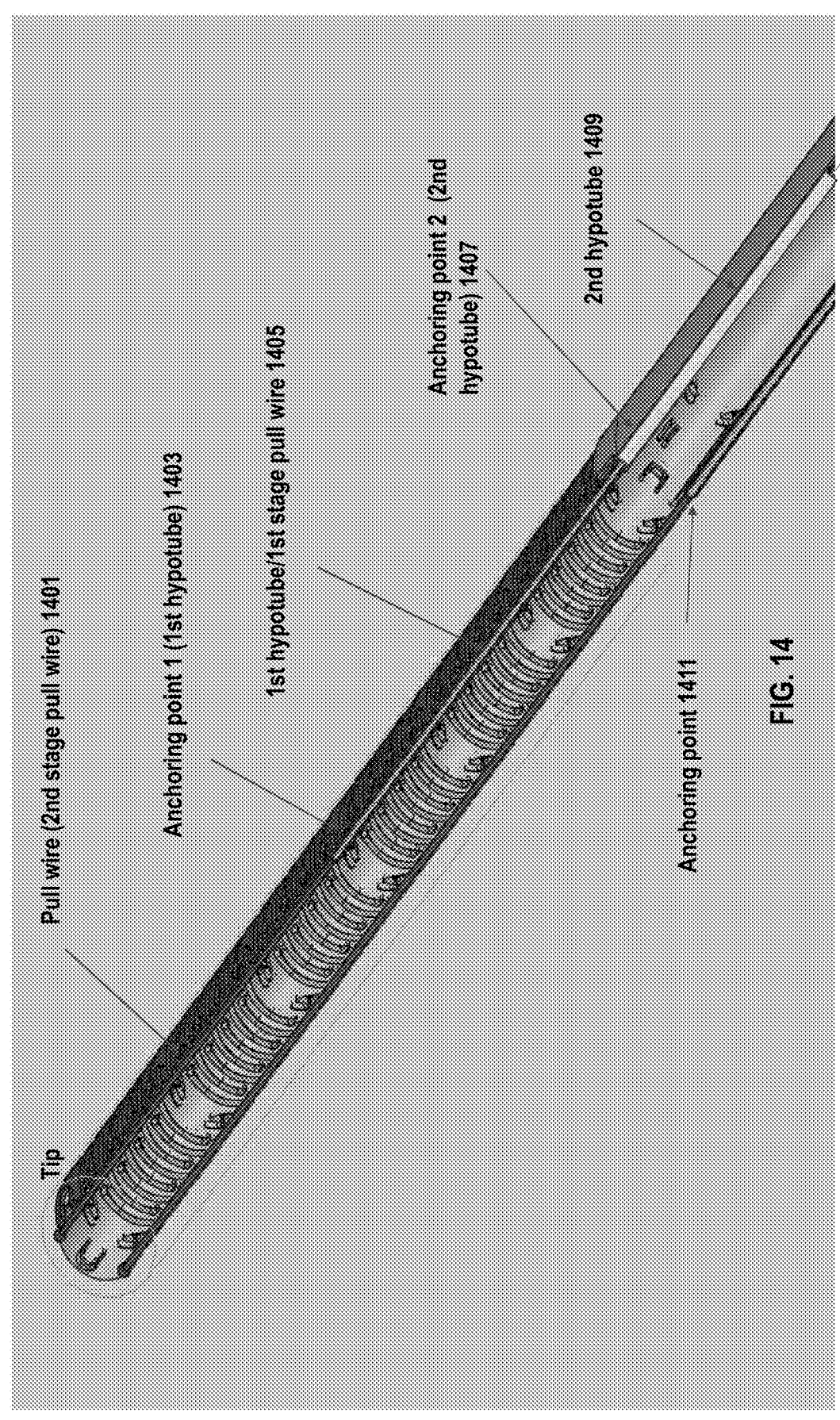
FIG. 14 shows an example of providing composite bending configurations.

FIG. 14 shows an example of providing composite bending configurations. In some embodiments, two or more hypotubes may be used for multiple bending stages. In the illustrated example, a first hypotube 1405 may be used as a first stage pull wire for the first stage bending. A pull wire 1401 (e.g., monofilament wire) may be used for the second stage bending. The first hypotube 1405 may have an anchoring point 1403 located at a first location (e.g., on the bending section) to provide a control end point for the pull wire 1401 thereby defining a first stage bending. The bending length of the first stage bending is between the anchoring point of the pull wire 1401 at the tip and the anchoring point 1403 of the first hypotube 1405. The bending length for the first bending stage may be adjusted by varying the anchoring point 1403 of the first hypotube. For example, the distal end of the first hypotube 1405 may be soldered or welded to the laser cut tube of the bending section at the anchoring point 1403.

A second hypotube 1409 may have an anchoring point 1407 located at a second location (e.g., on the shaft) to control the pull-wire-length of the first hypotube. The pull-wire-length is between the first anchoring point 1403 and the second anchoring point 1407.

The second hypotube 1409, the pull wire 1401 and the first hypotube 1405 may be substantially concentric. The first hypotube may be placed inside of the lumen of the second hypotube and may be slidable with respect to the second hypotube. When the first hypotube 1405 is pulled into the second hypotube 1409, the first hypotube 1405 may function as a first stage pull wire thereby changing the pull-wire-length between the first anchoring point 1403 and the second anchoring point 1407 resulting in different bending shapes.

The number of hypotubes corresponding to different directions may or may not be the same. For example, two hypotubes may be employed (e.g., first hypotube 1405 and second hypotube 1409 in a concentric configuration) for a first bending direction and a single hypotube may be used for a second bending direction. Additionally, the anchoring point of the hypotube 1411 for the second direction may or may not be the same as those for the first bending direction.

Figure 15:
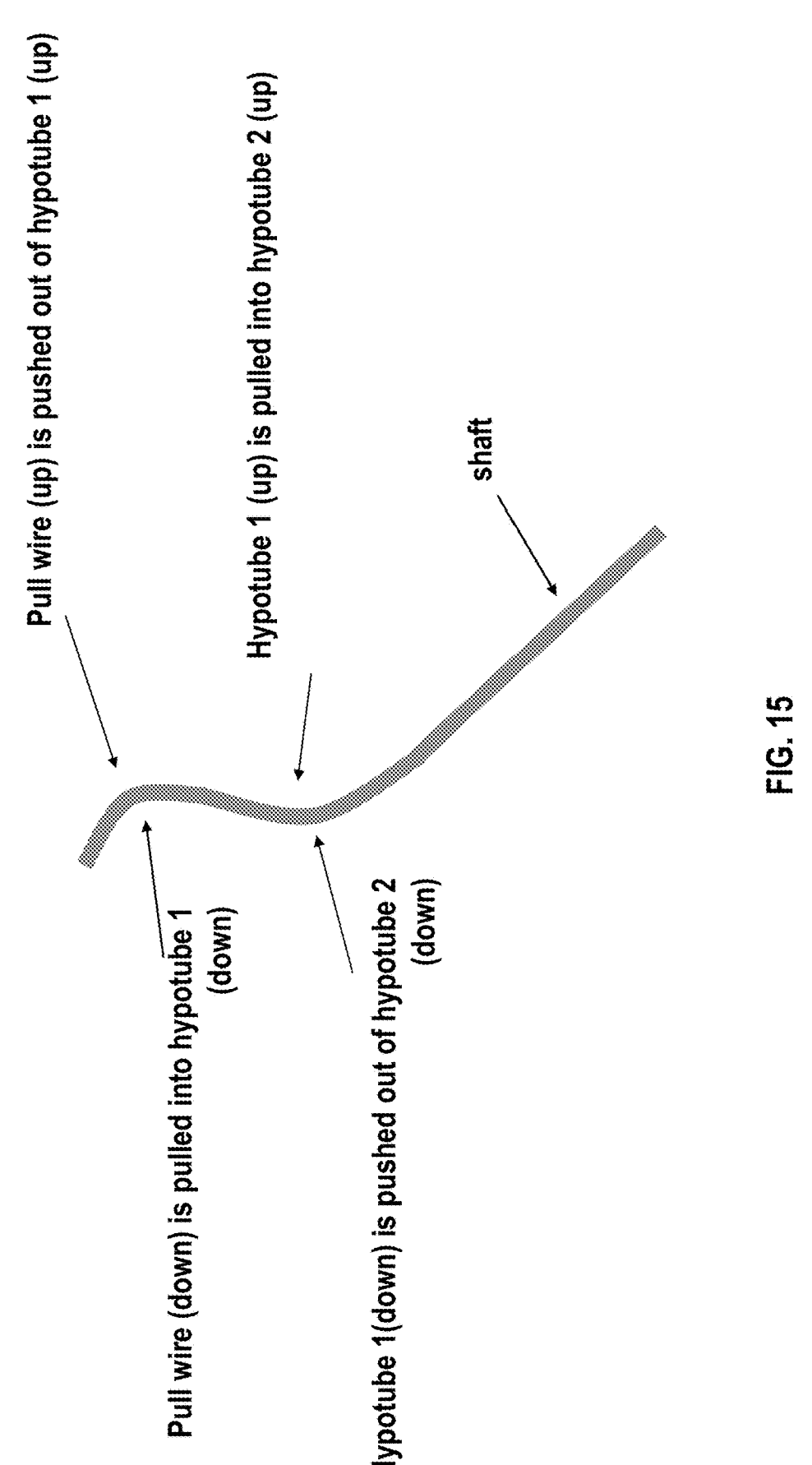
FIG. 15 schematically illustrates utilizing multiple hypotubes for composite curvatures.

FIG. 15 schematically illustrates utilizing multiple hypotubes for composite curvatures. In the illustrated example, an "S" curvature may be achieved by employing two hypotubes for a first direction (e.g., up) and two hypotubes for a second direction (e.g., down). By controlling the first hypotube to move relative to the second tube in a first direction/second direction, a composite bending configuration can be achieved. For instance, the shape may be achieved by pushing the pull wire out of the first hypotube and pulling the first hypotube into the second hypotube corresponding to the "up" direction, and pulling the pull wire into the first hypotube and pushing the first hypotube out of the second hypotube in the "down" direction.

In some embodiments, a proximal end of the tubes (e.g., hypotubes) may be anchored or fixed to the proximal portion of the catheter (e.g., handle). In some embodiments, the length of the tubes between distal anchoring point and the proximal anchoring point may be longer than the length of the flexible elongate member between the two anchoring points. For example, the length of the tubes may be at least 0.01%, 0.1%, 0.2%, 0.3%, 1%, 5%, 10% longer than the length of the corresponding portion of the flexible elongate member (e.g., shaft, bending section or a combination of both). For example, the tubes may have a spiral configuration that provides sufficient stiffness to bear/transmit the axial load. Similar to the load transmission tubes, the extra length of the tubes may beneficially accommodate the displacement within the flexible elongate member. Compared to existing techniques that may utilize coil pipes and service loop within the handle portion, the tubes herein may beneficially simplify the design, reduce the cost without compromising the bending performance of the catheter.

Figure 16:
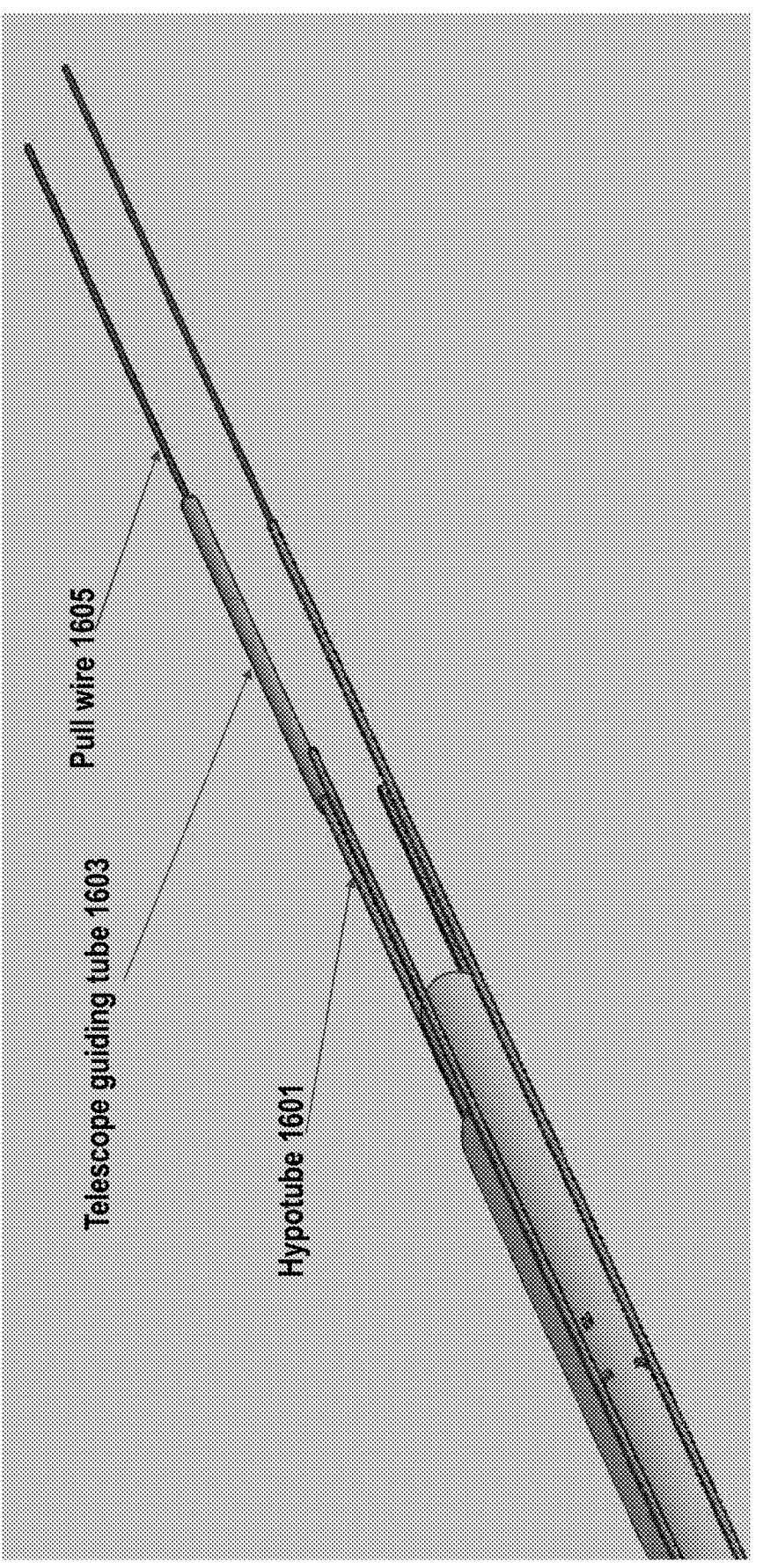
FIG. 16 shows an example of guiding tube at the proximal end of the catheter.
Figure 17:
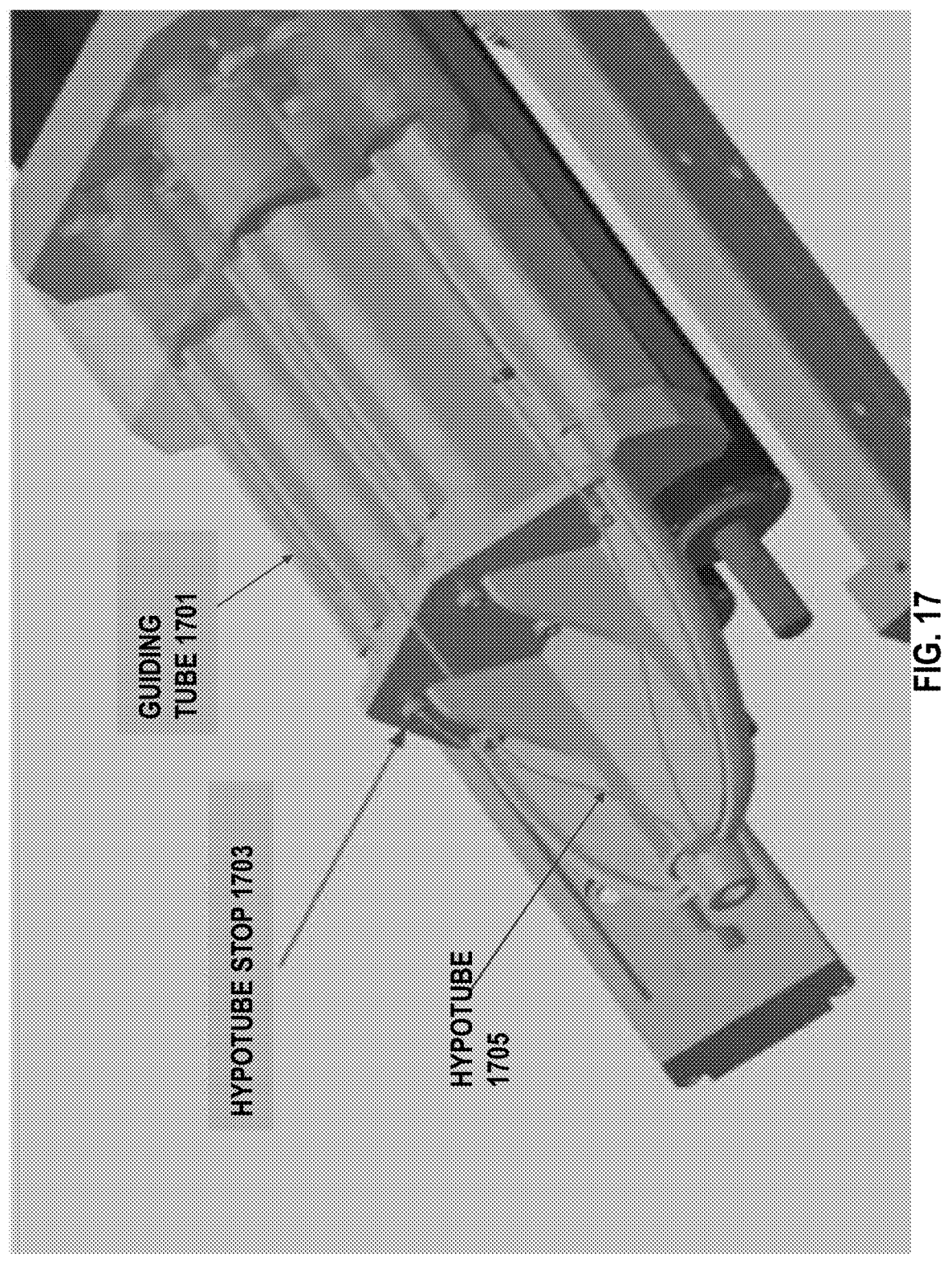
FIG. 17 shows a proximal end of a hypotube is fixed on the handle portion of the catheter at the hypotube stop.

In some embodiments, at the proximal end of the hypotube, a guiding tube may be utilized to facilitate guiding the collinear movement between the pull wire and the hypotube. FIGS. 16 and 17 show examples of guiding tubes at the proximal end. A guiding tube 1603 may slide over the hypotube 1601 to align the pull wire 1605 to the hypotube 1601. In some cases, the guiding tube 1603 may have a telescoping configuration to accommodate different distances between the proximal anchoring point of the hypotube and the proximal end of the pull wire. For example, telescope guiding tube may join with (e.g., fixedly connected to) the proximal end of the pull wire while providing clearance to slide over the hypotube.

FIG. 17 shows the proximal end of the hypotube 1705 is fixed on the handle portion of the catheter at a hypotube stop 1703. The proximal end of the hypotube may be aligned with the guiding tube 1701 allowing for a linear actuation movement by the motor.

Low Cost and Single Use Robotic Bronchoscope

In another aspect of the invention, a single-use robotic endoscope is provided. The robotic endoscope may be a bronchoscope and can be the same as the steerable catheter assembly as described elsewhere herein. Traditional endoscopes can be complex in design and are usually designed to be re-used after procedures, which require thorough cleaning, dis-infection, or sterilization after each procedure. The existing endoscopes are often designed with complex structures to ensure the endoscopes can endure the cleaning, dis-infection, and sterilization processes. The provided robotic bronchoscope can be a single-use endoscope that may beneficially reduce cross-contamination between patients and infections. In some cases, the robotic bronchoscope may be delivered to the medical practitioner in a pre-sterilized package and are intended to be disposed of after a single-use.

Figure 18:
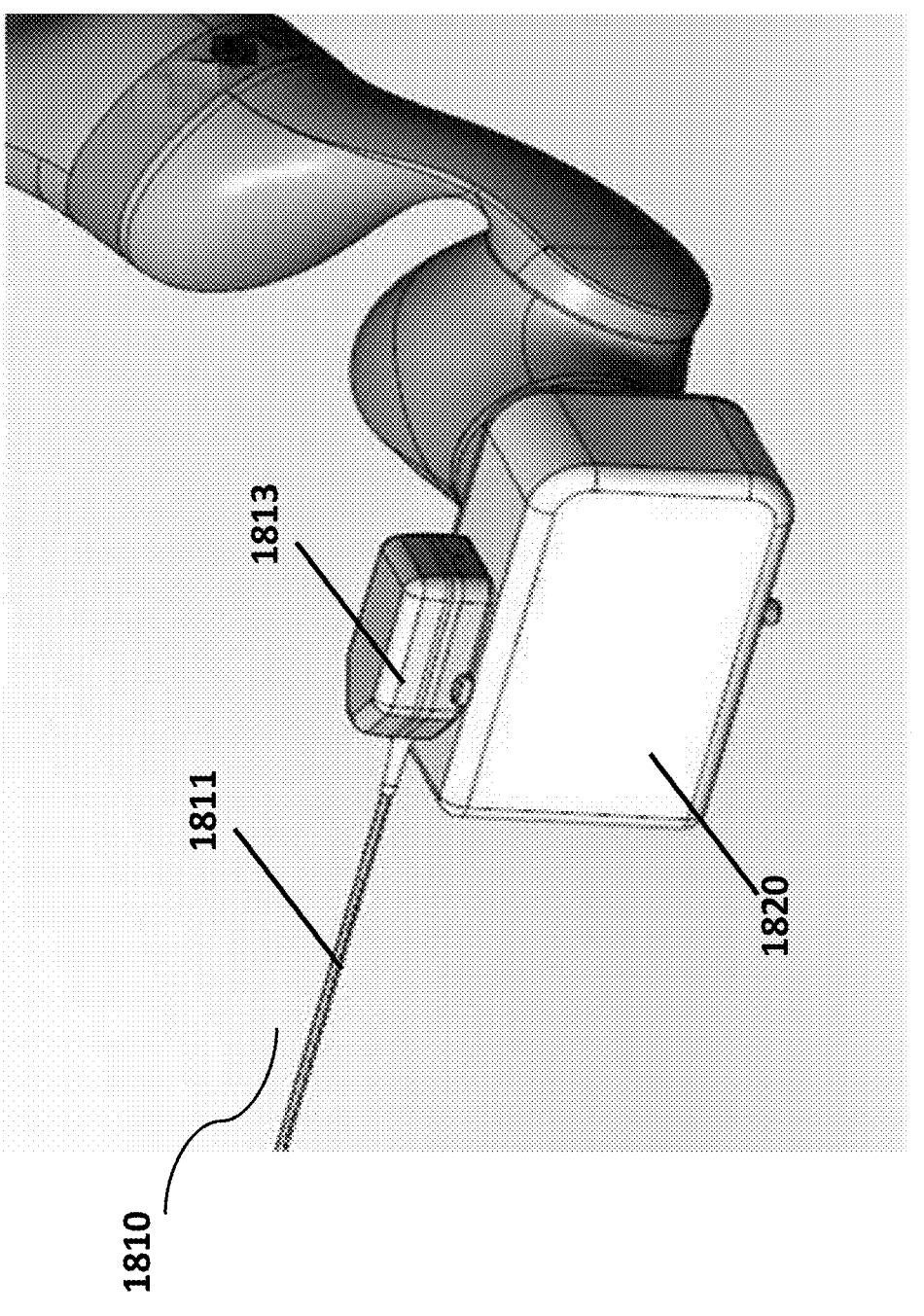
FIG. 18 shows an example of a robotic bronchoscope, in accordance with some embodiments of the invention.
Figure 19:
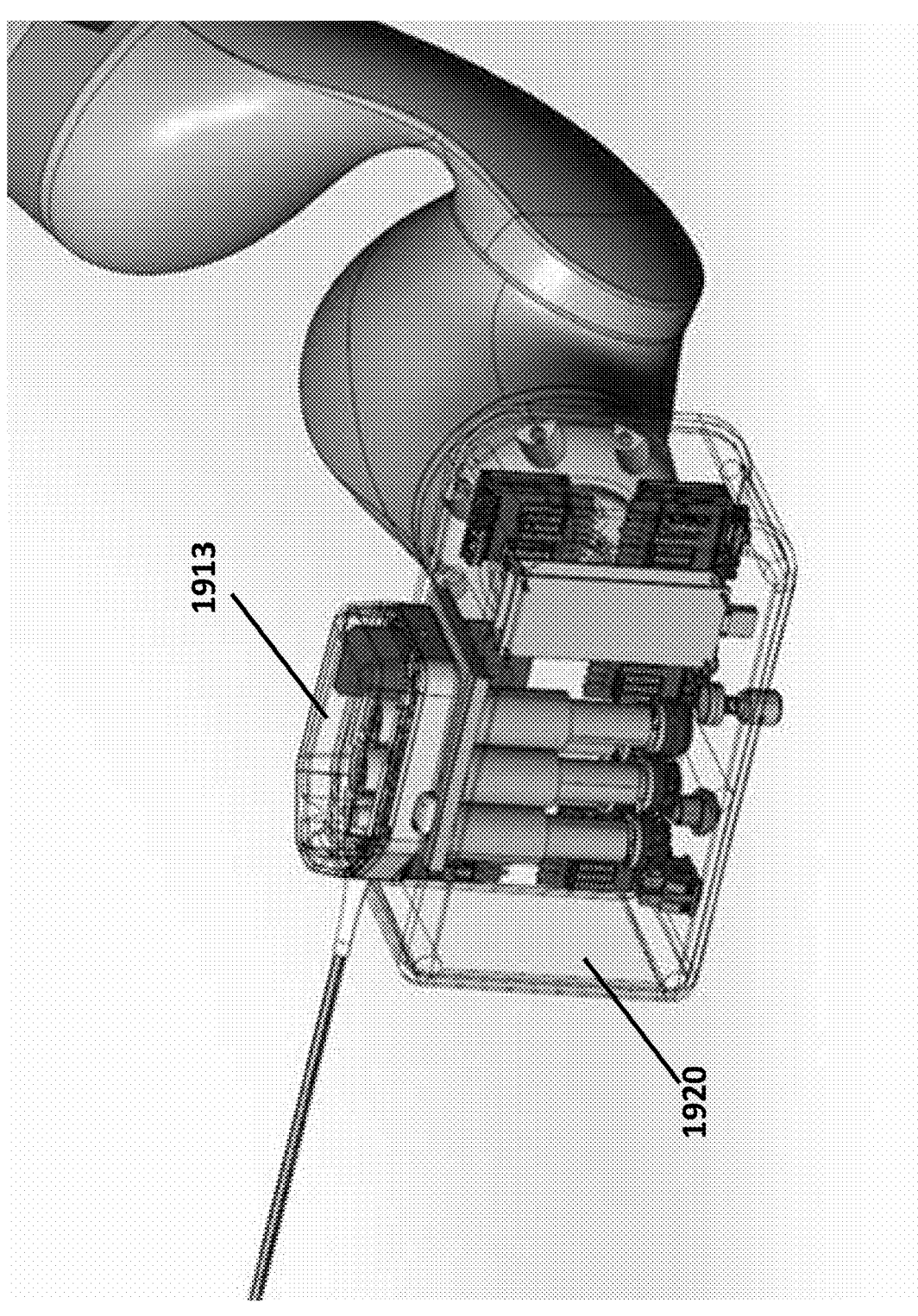
FIG. 19 shows an example of an instrument driving mechanism providing mechanical interface to a handle portion of a robotic bronchoscope, in accordance with some embodiments of the invention.
Figure 20:
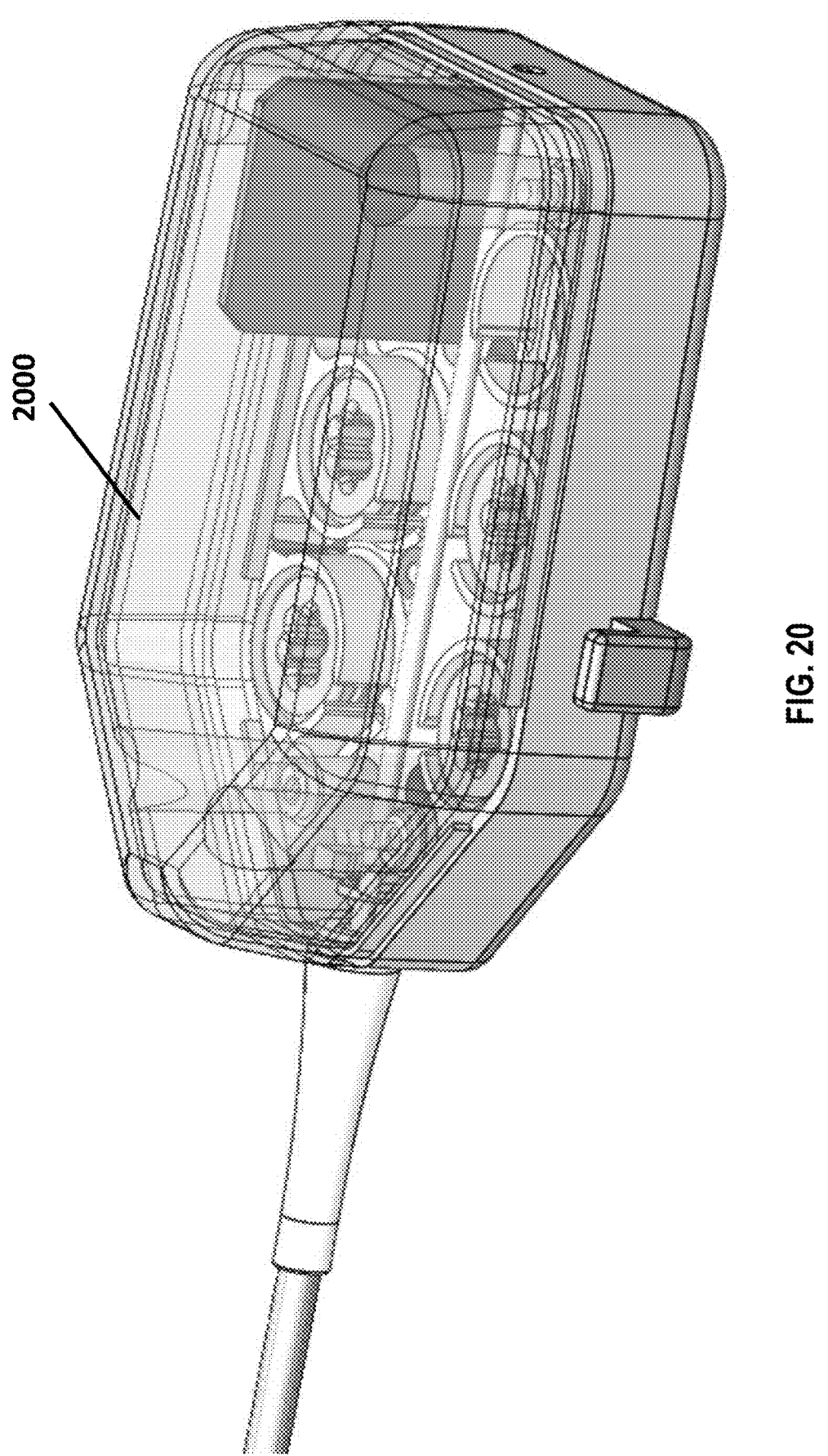
FIG. 20 shows an example handle portion of the robotic bronchoscope, in accordance with some embodiments of the invention.

FIGS. 18-20 show examples of a robotic bronchoscope, in accordance with some embodiments of the invention. As shown in FIG. 18, a robotic bronchoscope 1820 may comprise a handle portion 1813 and a flexible elongate member 1811. In some embodiments, the flexible elongate member 1811 may comprise a shaft, steerable tip and a steerable section. The robotic bronchoscope 1820 can be the same as the steerable catheter assembly as described in FIG. 1. The robotic bronchoscope may be a single-use robotic endoscope. In some cases, only the catheter may be disposable. In some cases, at least a portion of the catheter may be disposable. In some cases, the entire robotic bronchoscope may be released from the instrument driving mechanism and can be disposed of. The bronchoscope may contain varying levels of stiffness along its shaft, as to improve functional operation.

The robotic bronchoscope can be releasably coupled to an instrument driving mechanism 1820. The instrument driving mechanism 1820 may be mounted to the arm of the robotic support system or to any actuated support system as described elsewhere herein. The instrument driving mechanism may provide mechanical and electrical interface to the robotic bronchoscope 1820. The mechanical interface may allow the robotic bronchoscope 1820 to be releasably coupled to the instrument driving mechanism. For instance, the handle portion of the robotic bronchoscope can be attached to the instrument driving mechanism via quick install/release means, such as magnets and spring-loaded levels. In some cases, the robotic bronchoscope may be coupled or released from the instrument driving mechanism manually without using a tool.

FIG. 19 shows an example of an instrument driving mechanism 1920 providing mechanical interface to the handle portion 1913 of the robotic bronchoscope. As shown in the example, the instrument driving mechanism 1920 may comprise a set of motors that are actuated to rotationally drive a set of pull wires of the catheter. The handle portion 1913 of the catheter assembly may be mounted onto the instrument drive mechanism so that its pulley assemblies are driven by the set of motors. The number of pulleys may vary based on the pull wire configurations. In some cases, one, two, three, four, or more pull wires may be utilized for articulating the catheter.

The handle portion may be designed allowing the robotic bronchoscope to be disposable at reduced cost. For instance, classic manual and robotic bronchoscopes may have a cable in the proximal end of the bronchoscope handle. The cable often includes illumination fibers, camera video cable, and other sensors fibers or cables such as electromagnetic (EM) sensors, or shape sensing fibers. Such complex cable can be expensive adding to the cost of the bronchoscope. The provided robotic bronchoscope may have an optimized design such that simplified structures and components can be employed while preserving the mechanical and electrical functionalities. In some cases, the handle portion of the robotic bronchoscope may employ a cable-free design while providing a mechanical/electrical interface to the catheter.

FIG. 20 shows an example handle portion 2000 of the robotic bronchoscope, in accordance with some embodiments of the invention. In some case, the handle portion 2000 may be housing or comprise components configured to process image data, provide power, or establish communication with other external devices. In some cases, the communication may be wireless communication. For example, the wireless communications may include Wi-Fi, radio communications, Bluetooth, IR communications, or other types of direct communications. Such wireless communication capability may allow the robotic bronchoscope function in a plug-and-play fashion and can be conveniently disposed after single use. In some cases, the handle portion may comprise circuitry elements such as power sources for powering the electronics (e.g. camera and LED light source) disposed within the robotic bronchoscope or catheter.

The handle portion may be designed in conjunction with the catheter such that cables or fibers can be eliminated. For instance, the catheter portion may employ a design having a single working channel allowing instruments to pass through the robotic bronchoscope, as well as low cost electronics such as a chip-on-tip camera, illumination sources such as light emitting diode (LED) and EM sensors located at optimal locations in accordance with the mechanical structure of the catheter. This may allow for a simplified design of the handle portion. For instance, by using LEDs for illumination, the termination at the handle portion can be based on electrical soldering or wire crimping alone. For example, the handle portion may include a proximal board where the camera cable, LED cable, and EM sensor cable terminate while the proximal board connects to the interface of the handle portion and establishes the electrical connections to the instrument driving mechanism. As described above, the instrument driving mechanism is attached to the robot arm (robotic support system) and provides a mechanical and electrical interface to the handle portion. This may advantageously improve the assembly and implementation efficiency as well as simplify the manufacturing process and cost. In some cases, the handle portion along with the catheter may be disposed of after a single use.

Single-Use Steerable Catheter

Figure 21:
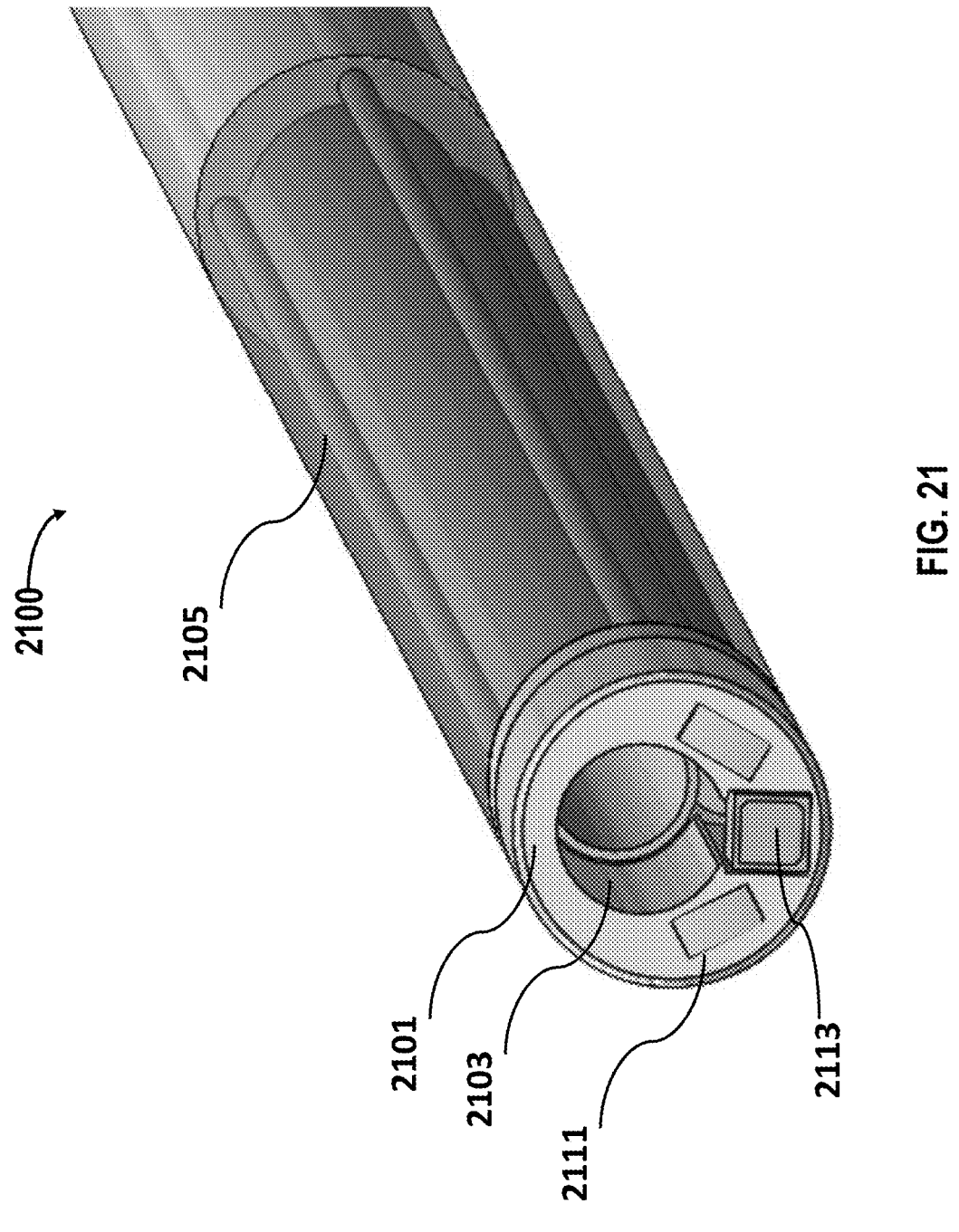
FIG. 21 shows an example steerable catheter, in accordance with some embodiments of the invention.

FIG. 21 shows an example steerable catheter 2100, in accordance with some embodiments of the invention. In some embodiments, the catheter may have a substantially integral design that one or more components may be integral to the catheter thereby simplifying the assembly, manufacturing process while preserving the kinematic, dynamic performance of the steerable catheter. As shown in the example, the steerable catheter may comprise an elongate member 2101 or a probing portion that is brought into proximity to the tissue and/or area that is to be examined. The elongate member 2101 may, in some cases, also be referred to as catheter. The catheter 2101 may comprise internal structures such as a working channel 2103 allowing tools as described elsewhere herein to be inserted through. In some cases, the working channel may have a dimension such as diameter of around 2 mm to be compatible with standard tools.

The catheter 2101 may be composed of suitable materials for desired flexibility or bending stiffness. In some cases, the materials of the catheter may be selected such that it may maintain structural support to the internal structures (e.g., working channel) as well as being substantially flexible (e.g., able to bend in various directions and orientations). For example, the catheter can be made of any suitable material such as Provista Copolymer, vinyl (such as polyvinyl chloride), Nylon (such as vestamid, grilamid), pellethane, polyethylene, polypropylene, polycarbonate, polyester, silicon elastomer, acetate and so forth. In some cases, the materials may be polymer material, biocompatible polymer material and the catheter may be sufficiently flexible to be advancing through a path with a small curvature without causing pain to a subject. In some cases, the catheter may comprise a sheath. The sheath may not be the same length of the catheter. The sheath may be shorter than the catheter to provide desired support. Alternatively, the catheter may be substantially a single-piece component.

In some cases, the distal portion or tip of the catheter may be substantially flexible such that it can be steered into one or more directions (e.g., pitch, yaw). The catheter may comprise a tip portion, bending section, and insertion shaft same as those as described above. In some embodiments, the catheter may have variable bending stiffness along the longitudinal axis direction. For instance, the catheter may comprise multiple segments having different bending stiffness (e.g., flexible, semi-rigid, and rigid). The bending stiffness may be varied by selecting materials with different stiffness/rigidity, varying structures in different segments (e.g., cuts, patterns), adding additional supporting components or any combination of the above. In some cases, a proximal end of the catheter needs not be bent to a high degree thus the proximal portion of the catheter may be reinforced with additional mechanical structure (e.g., additional layers of materials) to achieve a greater bending stiffness. Such design may provide support and stability to the catheter. In some cases, the variable bending stiffness may be achieved by using different materials during extrusion of the catheter. This may advantageously allow for different stiffness levels along the shaft of the catheter in an extrusion manufacturing process without additional fastening or assembling of different materials.

The distal portion of the catheter may be steered by one or more pull wires 2105. The distal portion of the catheter may be made of any suitable material such as co-polymers, polymers, metals or alloys such that it can be bent by the pull wires. In some embodiments, the proximal end or portion of one or more pull wires 2105 may be operatively coupled to various mechanisms (e.g., gears, pulleys, etc.) in the handle portion of the catheter assembly. The pull wire 2105 may be a metallic wire, cable or thread, or it may be a polymeric wire, cable or thread. The pull wire 2105 can also be made of natural or organic materials or fibers. The pull wire 2105 can be any type of suitable wire, cable or thread capable of supporting various kinds of loads without deformation, significant deformation, or breakage. The distal end or portion of one or more pull wires 2105 may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

As described above, the pull wires may be made of any suitable material such as stainless steel (e.g. SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals. Pull wires may run through the lumen of one or more load transmission tubes and/or hypotubes as described elsewhere herein.

The catheter may have a dimension so that one or more electronic components can be integrated to the catheter. For example, the outer diameter of the distal tip may be around 4 to 4.4 millimeters (mm), and the diameter of the working channel may be around 2 mm such that one or more electronic components can be embedded into the wall of the catheter. However, it should be noted that based on different applications, the outer diameter can be in any range smaller than 4 mm or greater than 4.4 mm, and the diameter of the working channel can be in any range according to the tool dimensional or specific application.

The one or more electronic components may comprise an imaging device, illumination device or sensors. In some embodiments, the imaging device may be a video camera 2113. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources 2111 positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting.

The imaging device and the illumination device may be integrated to the catheter. For example, the distal portion of the catheter may comprise suitable structures matching at least a dimension of the imaging device and the illumination device. The imaging device and the illumination device may be embedded into the catheter. FIG. 22 shows an example distal portion of the catheter with integrated imaging device and the illumination device. A camera may be located at the distal portion. The distal tip may have a structure to receive the camera, illumination device and/or the location sensor. For example, the camera may be embedded into a cavity 2210 at the distal tip of the catheter. The cavity 2210 may be integrally formed with the distal portion of the cavity and may have a dimension matching a length/width of the camera such that the camera may not move relative to the catheter. The camera may be adjacent to the working channel 2220 of the catheter to provide near field view of the tissue or the organs. In some cases, the attitude or orientation of the imaging device may be controlled by controlling a rotational movement (e.g., roll) of the catheter.

The power to the camera may be provided by a wired cable. In some cases, the cable wire may be in a wire bundle providing power to the camera as well as illumination elements or other circuitry at the distal tip of the catheter. The camera and/or light source may be supplied with power from a power source located at the handle portion via wires, copper wires, or via any other suitable means running through the length of the catheter. In some cases, real-time images or video of the tissue or organ may be transmitted to an external user interface or display wirelessly. The wireless communication may be WiFi, Bluetooth, RF communication or other forms of communication. In some cases, images or videos captured by the camera may be broadcasted to a plurality of devices or systems. In some cases, image and/or video data from the camera may be transmitted down the length of the catheter to the processors situated in the handle portion via wires, copper wires, or via any other suitable means. The image or video data may be transmitted via the wireless communication component in the handle portion to an external device/system. In some cases, the system may be designed such that no wires are visible or exposed to operators.

In conventional endoscopy, illumination light may be provided by fiber cables that transfer the light of a light source located at the proximal end of the endoscope, to the distal end of the robotic endoscope. In some embodiments of the disclosure, miniaturized LED lights may be employed and embedded into the distal portion of the catheter to reduce the design complexity. In some cases, the distal portion may comprise a structure 2230 having a dimension matching a dimension of the miniaturized LED light source. As shown in the illustrated example, two cavities 2230 may be integrally formed with the catheter to receive two LED light sources. For instance, the outer diameter of the distal tip may be around 4 to 4.4 millimeters (mm) and diameter of the working channel of the catheter may be around 2 mm such that two LED light sources may be embedded at the distal end. The outer diameter can be in any range smaller than 4 mm or greater than 4.4 mm, and the diameter of the working channel can be in any range according to the tool's dimensional or specific application. Any number of light sources may be included. The internal structure of the distal portion may be designed to fit any number of light sources.

In some cases, each of the LEDs may be connected to power wires which may run to the proximal handle. In some embodiment, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out. In some cases, an additional cover 2231 may be placed at the forwarding end face of the distal tip providing precise positioning of the LEDs as well as sufficient room for the glue. The cover 2231 may be composed of transparent material matching the refractive index of the glue so that the illumination light may not be obstructed.

Figure 23:
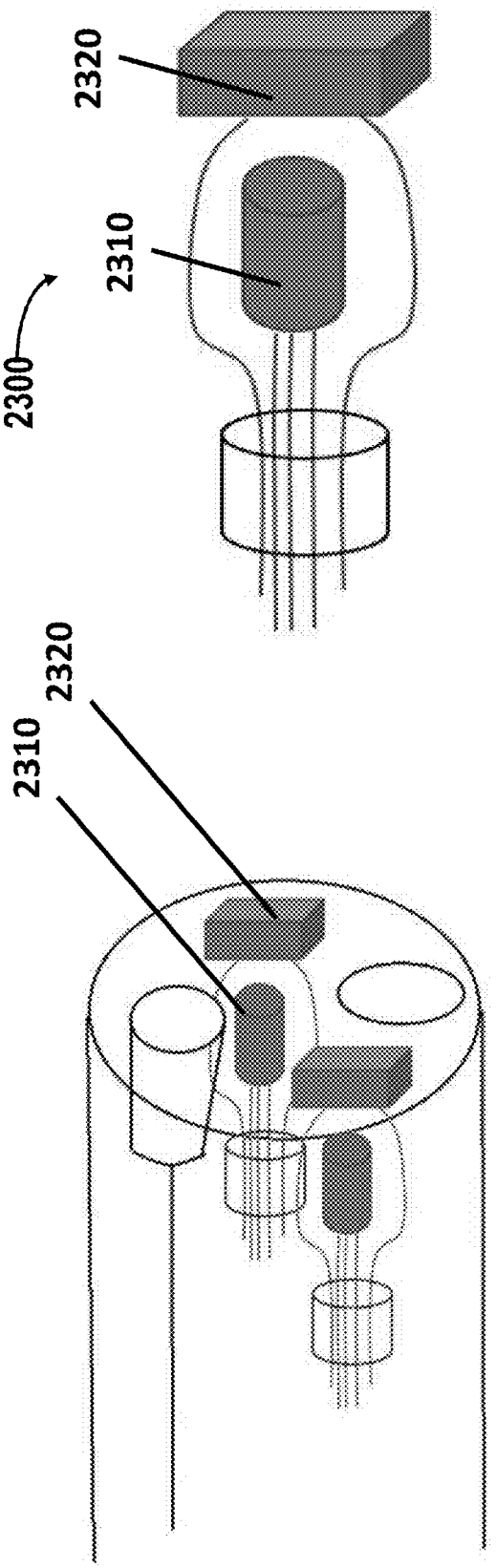
FIG. 23 shows an example of a compact configuration of a plurality of electronic elements disposed at a distal portion of a catheter, in accordance with some embodiments of the invention.

In some embodiments, one or more sensors may be embedded into the distal portion of the catheter. In conventional robotic bronchoscopes, sensors may be used to track the tip position which are usually located at the distal tip thereby causing an increased size of the tip. The provided steerable catheter may bundle one or more electronic components to provide a compact design. In some cases, the illumination light source and one or more position sensors may be combined into a bundle. FIG. 23 shows an example of a compact configuration of the electronic elements located at the distal portion. In some embodiments, position sensors such as electromagnetic (EM) sensors may be used to accurately track the position of the distal tip of the catheter. For example, electromagnetic coils 2310 located on the distal end may be used with the electromagnetic tracking system to detect the position and orientation of the distal tip of the catheter while it is disposed within an anatomical system (e.g., anatomical luminal network). In some cases, the coils may be angled to provide sensitivity to electromagnetic fields along different axes, giving the disclosed navigational systems the ability to measure a six-degrees of freedom: three positional and three angular.

In some cases, one or more EM sensors 2310 may be located at the distal portion and may be placed adjacent to or behind the illumination light sources 2320 (e.g., LEDs) in a stereoscopic arrangement. In some cases, an EM sensor and a LED light source may form a bundle 2300. The power cables of the EM sensors may be bundled together with the wires of the LEDs to provide reduced space and complexity. In some cases, the stereoscopic alignment may provide differential 5D measurement, or a fused 6D measurement, that allows accurate positioning and orientation-sensing of the catheter distal tip. During the procedure, the EM field generator positioned next to, under, or above, a patient torso may locate the EM sensors thereby tracking the location of the catheter tip in real-time.

Pull Wire Configurations and Design

Figure 24:
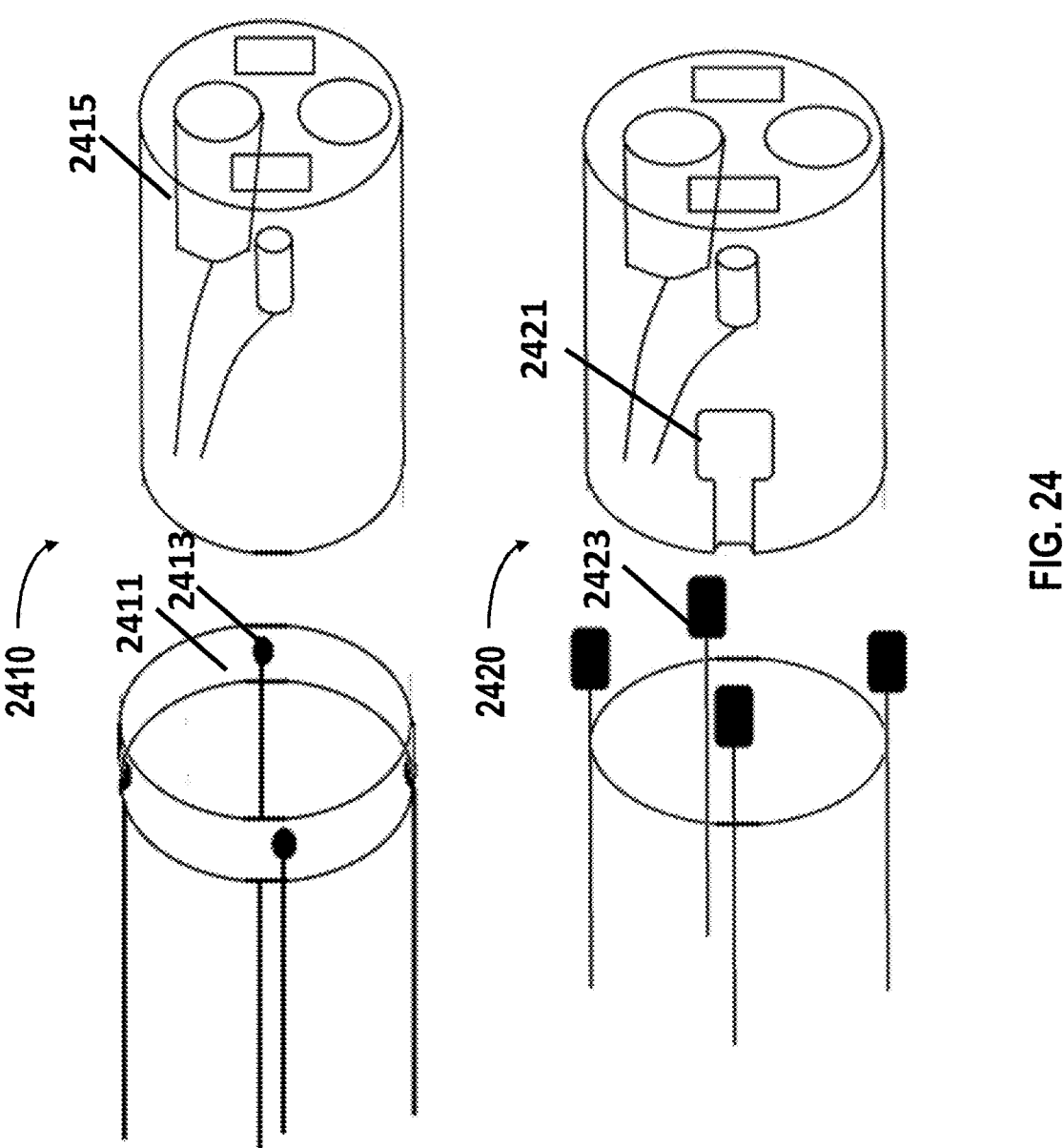
FIG. 24 shows an example of a conventional configuration of pull wires attached to a control ring structure and a novel configuration of the present disclosure.

The robotic endoscope (e.g., bronchoscope) may comprise one or more pull wires for controlling articulation of the catheter. In conventional endoscopes, the distal end or portion of the one or more pull wires may be anchored or mounted to a control ring, such that operation of the pull wires by the control unit may apply force or tension to the control ring which may steer or articulate (e.g., up, down, pitch, yaw, or any direction in-between) certain section or portion (e.g., distal section) of the catheter. FIG. 24 shows an example of a conventional configuration of pull wires 2413 attached to a control ring structure 2411 and a novel configuration 2420 of the present disclosure. The control ring may be attached to the distal end of the catheter 2415. Usually the tip of the pull wires is welded or soldered to the control ring 2411 and the control ring may also be attached to the distal tip by welding. The welding process can be costly, cumbersome and complex. Moreover, when one pull wire is broken or malfunctions, the entire steering control functionality may be affected.

The provided robotic endoscope (e.g., bronchoscope) may comprise individually controlled pull wires each of which is connected to the distal portion directly. As shown in the example 2420, the one or more pull wires 2423 may be attached to an integrally formed structure 2421 of the distal portion. For example, the integrally formed structure 2421 may be grooves that are molded with the distal tip. The grooves may have a dimension or size that match the dimension of the distal end 2421 of the pull wire such that the pull wire can be conveniently crimped at distal end. This may advantageously improve the assembly efficiency. In some instances, the pull wires may be rigidly affixed to the grooves at the distal end such that the distal end of the pull wire may not be permitted to move relative to the distal portion of the catheter.

The pull wire configuration may also provide improved reliability in steering the distal portion. For instance, as each pull wire is individually connected to the distal portion and individually controlled, the articulation force may be dynamically adjusted according to different pull wire configurations. For instance, the articulation force may be recalculated and the control signals for controlling the pull wires may be dynamically adjusted based on the available pull wires in case a pull wire is broken.

Figure 25:
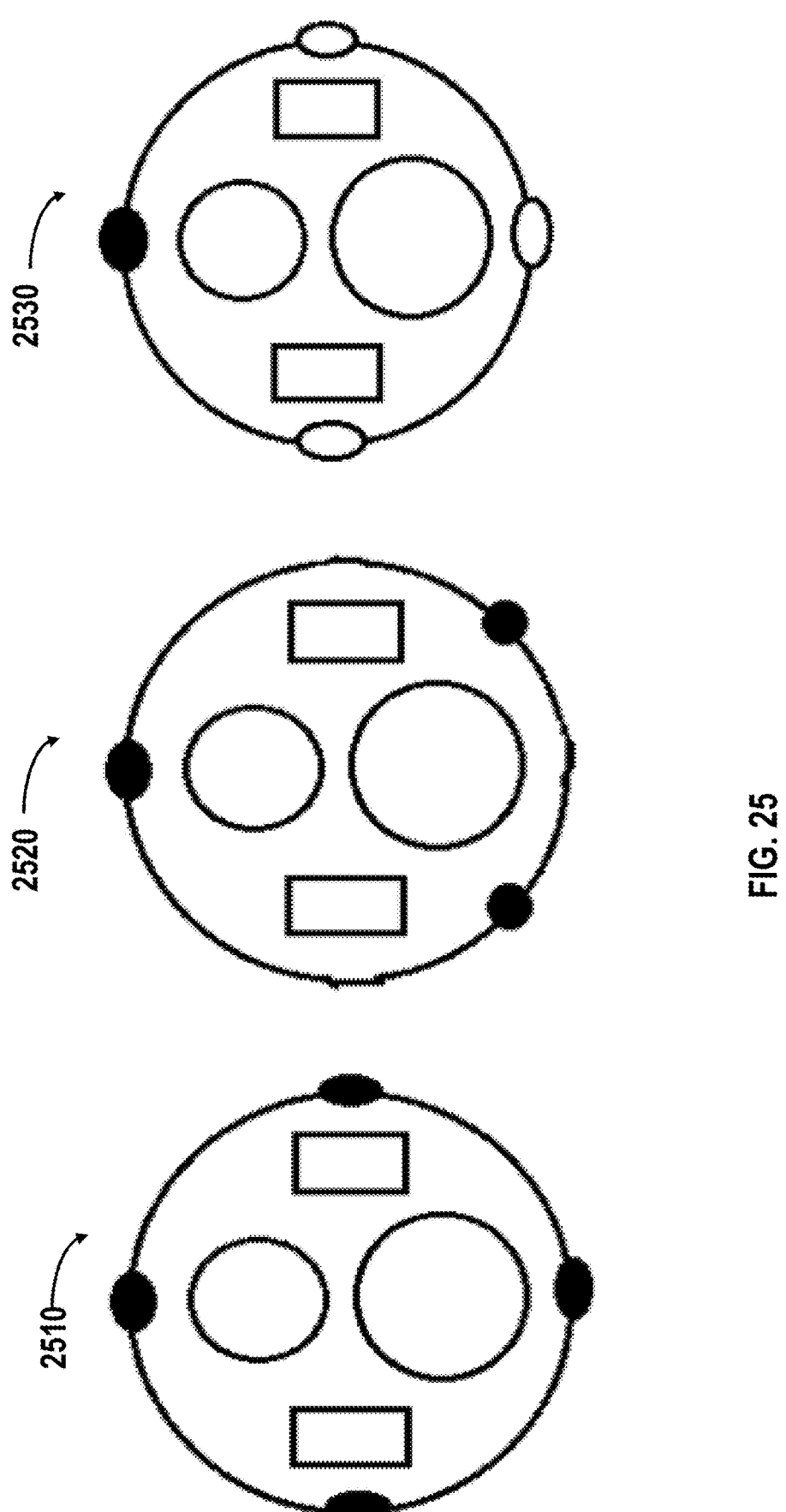
FIG. 25 shows various configurations of pull wires for a robotic catheter system, in accordance with some embodiments of the invention.

The convenient assembly of pull wires to the distal portion may also allow for flexibility in designing pull wire configurations. For example, the number or combination of pull wires can be selected or adjusted dynamically to meet different performance or design requirements. FIG. 25 shows various configurations of pull wires for a robotic catheter system. In some embodiments, the integral structure (grooves) for receiving the pull wires may be pre-fabricated. For example, four grooves may be integrally formed with the catheter and one or more pull wires may be fixedly connected/crimped to one or more grooves selected from the plurality of grooves to form different configurations 2510, 2530. As shown in the example, any number of grooves/slots or any given subset of grooves/slots can be selected to receive or couple to the pull wires at one end. In some cases, once a combination of slots/grooves is selected to be coupled to the corresponding pull wires, a pull-wire configuration pattern may be formed and a mapping relationship between the selected grooves/slots and the pull wires may be transmitted to the control unit. Control signals may then be generated during articulation based on the mapping relationship to achieve desired articulation force.

In another example, the pre-fabricated grooves may have various configurations. For instance, a three-pull-wire configuration 2520 may have three grooves separated by about 120°. In some cases, a virtual mapping algorithm may map the three-wire configuration to a four-wire configuration. The virtual mapping algorithm can also be utilized to update a new mapping relationship when one or more pull wires are malfunctioning/broken during operation. Such integral design of the pull wire configurations advantageously simplifies the assembly, manufacturing process while preserving the kinematic, dynamic performance of the catheter.

Guidewire with an Inflatable Tip

In some embodiments, a guidewire may be used during bronchoscopy operation. A guidewire may usually be inserted far beyond the tip of the bronchoscope to enter the desired air passageway first, and subsequently allow the bronchoscope to slide over the guidewire into the selected passage. Due to the guidewire's smaller diameter in comparison to that of a bronchoscope, the guidewire may not have sufficient stiffness and/or enough frictional force to anchor the guidewire within the air passages.

Figure 26:
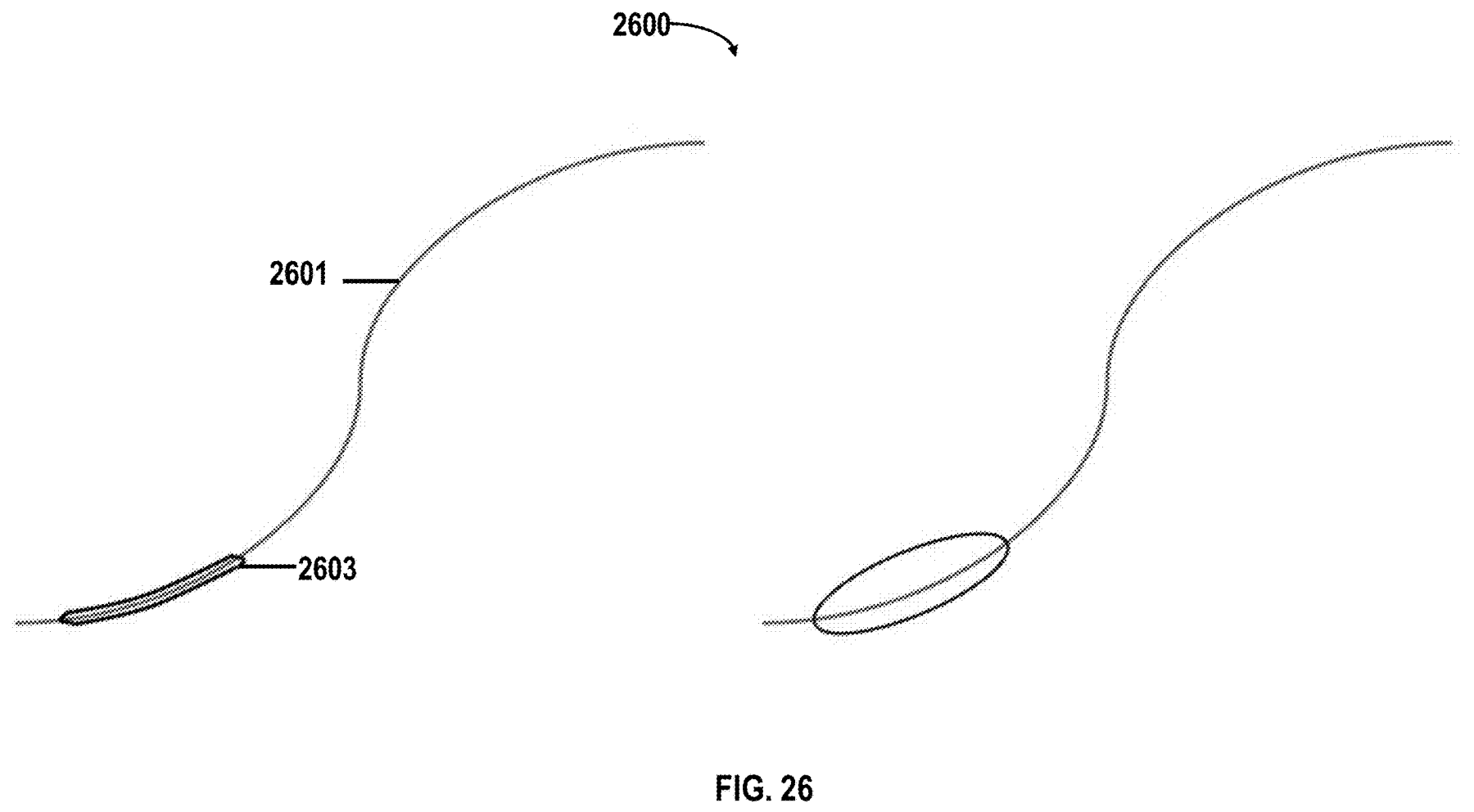

The guidewire of the present disclosure may have an expandable outside diameter feature at the tip. FIG. 26 shows an example of a guidewire 2600 with inflatable tips. The guidewire 2601 may be inserted through the working channel of the catheter/bronchoscope to assist in navigation of the air passages in the lung. In some cases, the guidewire may be extended past the tip of the catheter into the desired airway and the catheter may then slide over the guidewire to reach the desired location. The inflatable tip can be implemented using various suitable methods. For example, an additional component 2603 such as an inflatable balloon may be positioned at or close to the distal end of the guidewire. The balloon may be connected through the working channel to a balloon inflation source or pump for inflation or deflation of the balloon.

In some cases, the guidewire may comprise perforated holes. The diameter of the deflated balloon may be equal to the diameter of the elongate arm (e.g. bronchoscope catheter). In some cases, the diameter of the deflated balloon may be slightly greater than the elongate arm. The guidewire may be able to move distally or proximally. The guidewire may be attached to an air pump to inject and withdraw the air from the guidewire, which consequently inflates and deflates the balloon respectively. During the insertion of guidewire into the airway, the balloon may remain deflated. while the proper location is reached, the balloon will be inflated by pumping in the air. Once the bronchoscope reaches the desired forward position, the balloon may be deflated by pumping the air out that may allow the guidewire to move forward. In some embodiments, the inflatable tip can be made of collapsible mesh structures using materials, such as shape memory alloy (SMA), electro-active polymer (EAP), and ferromagnetic fluids, with its corresponding inflation and deflation control mechanisms. The anchoring element can have any other form to secure the anchoring of the guidewire. For example, the anchoring element may be metal wires that can expand or collapse radially. The anchoring element may be actuated by a slide actuator that is slid linearly to cause the anchoring element to change its position and in particular, to cause the anchoring element to either deploy or to be placed back into a collapsed position. The sliding action of the actuator may be translated into a change in the position (condition) of the anchoring element (e.g., anchoring element deploys and radially expands so as to provide a structure that anchors the guidewire in place, or conversely, anchoring element radially contracts and is returned to a collapsed state.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An articulating flexible endoscope comprising:
a bending section connected to a distal tip portion of the articulating flexible endoscope at a first end, and connected to a shaft portion of the articulating flexible endoscope at a second end, wherein at least a portion of the articulating flexible endoscope is disposable;
a pull wire coupled to the distal tip portion at a first location and is configured for articulating the bending section; and
a first tube for accommodating the pull wire and is concentric with the pull wire, wherein a distal end of the first tube is coupled to a second location on the bending section or on the shaft portion, wherein a proximal end of the first tube is coupled to a proximal portion of the articulating flexible endoscope and wherein the first tube is a hypotube and a wall thickness or a material of the hypotube is selected to transmit articulation reaction loads from the bending section to the proximal portion of the articulating flexible endoscope,
wherein an effective bending section of the articulating flexible endoscope is adjusted by varying i) a length between the first location and the second location or ii) the second location.

2. The articulating flexible endoscope of claim 1, further comprising a second tube coupled to the articulating flexible endoscope at a third location, and wherein the first tube, the second tube and the pull wire are concentric.

3. The articulating flexible endoscope of claim 2, wherein the effective bending section comprises a first stage bending defined by the first location and the second location, and a second stage bending defined by the second location and the third location.

4. The articulating flexible endoscope of claim 1, wherein the distal tip portion comprises a structure to receive an imaging device, a position sensor, an illumination device.

5. The articulating flexible endoscope of claim 1, wherein the pull wires is placed inside of a lumen of the first tube.

6. The articulating flexible endoscope of claim 1, wherein the effective bending section is bent by the pull wire in a corresponding bending direction.

7. The articulating flexible endoscope of claim 1, wherein the first tube has a length greater than the length of the corresponding portion of the articulating flexible endoscope.

8. The articulating flexible endoscope of claim 1, wherein the first tube has a non-straight configuration.

9. The articulating flexible endoscope of claim 1, wherein the first tube has a spiral configuration.

10. The articulating flexible endoscope of claim 1, further comprising a guiding tube for guiding the pull wire to be aligned with the first tube at the proximal end of the first tube.

11. The articulating flexible endoscope of claim 10, wherein the guiding tube is a telescoping tube.

12. The articulating flexible endoscope of claim 1, wherein the bending section comprises an inner tube having a plurality of tabs formed on an external surface of the inner tube.

13. The articulating flexible endoscope of claim 12, wherein the plurality of tabs are configured to constrain the pull wire within a space.

14. The articulating flexible endoscope of claim 12, wherein the distal end of the first tube is coupled to the inner tube.

15. The articulating flexible endoscope of claim 1, wherein the bending section comprises an outer tube having a plurality of tabs formed on an internal surface of the outer tube.

16. The articulating flexible endoscope of claim 1, wherein the pull wire has relative movement with respect to the first tube.

17. The articulating flexible endoscope of claim 1, wherein the entire articulating flexible endoscope is disposable.

18. A method for providing a configurable bending section for an endoscope, the method comprising:
providing a bending section, wherein the bending section is connected to a distal tip portion of the endoscope at a first end and a shaft portion of the endoscope at a second end;
coupling a pull wire to the distal tip portion at a first location, wherein the pull wire is configured for articulating the bending section, wherein the pull wire is accommodated by a first tube, and wherein the pull wire and the first tube are concentric; and
coupling a distal end of the first tube to a second location on the bending section or on the shaft portion and coupling a proximal end of the first tube to a proximal portion of the endoscope, wherein the first tube is a hypotube and a wall thickness or a material of the hypotube is selected to transmit articulation reaction loads from the bending section to the proximal portion of the endoscope,
wherein an effective bending section of the endoscope is adjusted by varying i) a length between the first location and the second location or ii) the second location.

19. The method of claim 18, wherein the pull wires is placed inside of a lumen of the first tube and has a relative movement with respect to the first tube.

* * * * *